US007846936B2

(12) United States Patent
Hilberg et al.

(10) Patent No.: US 7,846,936 B2
(45) Date of Patent: Dec. 7, 2010

(54) COMBINATIONS FOR THE TREATMENT OF DISEASES INVOLVING CELL PROLIFERATION, MIGRATION OR APOPTOSIS OF MYELOMA CELLS OR ANGIOGENESIS

(75) Inventors: Frank Hilberg, Vienna (AT); Flavio Solca, Vienna (AT); Anke Baum, Vienna (AT); Jacobus C. A. van Meel, Moedling (AT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 12/140,661

(22) Filed: Jun. 17, 2008

(65) Prior Publication Data

US 2008/0254040 A1     Oct. 16, 2008

Related U.S. Application Data

(63) Continuation of application No. 10/830,147, filed on Apr. 22, 2004, now abandoned.

(60) Provisional application No. 60/542,036, filed on Feb. 5, 2004.

(30) Foreign Application Priority Data

Apr. 29, 2003  (EP)  .................... 03009587
Jan. 13, 2004  (EP)  .................... 04000508
Jan. 21, 2004  (EP)  .................... 04001171

(51) Int. Cl.
    *A61K 31/497*   (2006.01)
(52) U.S. Cl. ................ 514/254.09; 514/266.24
(58) Field of Classification Search ............. 514/254.09, 514/266.24
    See application file for complete search history.

(56) References Cited

U.S. PATENT DOCUMENTS

| 6,306,874 | B1 | 10/2001 | Fraley et al. |
| 6,762,180 | B1 | 7/2004 | Roth et al. |
| 6,794,393 | B1 | 9/2004 | Fraley et al. |
| 7,019,012 | B2 | 3/2006 | Himmelsbach et al. |
| 7,220,750 | B2 | 5/2007 | Himmelsbach et al. |
| 2002/0169180 | A1 | 11/2002 | Himmelsbach et al. |
| 2002/0173509 | A1 | 11/2002 | Himmelsbach et al. |
| 2003/0069299 | A1 | 4/2003 | Walter et al. |
| 2003/0108545 | A1 | 6/2003 | Rockwell et al. |
| 2003/0119819 | A1 | 6/2003 | Liang et al. |
| 2003/0225079 | A1 | 12/2003 | Singer et al. |
| 2004/0127453 | A1 | 7/2004 | Lyons et al. |
| 2004/0176392 | A1 | 9/2004 | Roth et al. |
| 2005/0043233 | A1 | 2/2005 | Stefanic et al. |
| 2005/0085495 | A1 | 4/2005 | Soyka et al. |
| 2006/0058311 | A1 | 3/2006 | Munzert et al. |
| 2006/0100223 | A1 | 5/2006 | Himmelsbach et al. |
| 2007/0027170 | A1 | 2/2007 | Soyka et al. |
| 2007/0099918 | A1 | 5/2007 | Singer et al. |
| 2007/0185091 | A1 | 8/2007 | Himmelsbach et al. |
| 2008/0254040 | A1 | 10/2008 | Stefanic et al. |
| 2009/0238828 | A1 | 9/2009 | Munzert et al. |
| 2009/0306044 | A1 | 12/2009 | Solca et al. |
| 2009/0306101 | A1 | 12/2009 | Solca et al. |
| 2009/0306378 | A1 | 12/2009 | Schroeder et al. |
| 2009/0318480 | A1 | 12/2009 | Solca |
| 2010/0069414 | A1 | 3/2010 | Himmelsbach et al. |
| 2010/0144639 | A1 | 6/2010 | Singer et al. |

FOREIGN PATENT DOCUMENTS

| CA | 2 387 013 A1 | 4/2001 |
| CA | 2 432 428 A1 | 6/2002 |
| CA | 2 493 310 A1 | 2/2004 |
| DE | 199 24 401 A1 | 11/2000 |
| DE | 100 42 696 A1 | 3/2002 |
| DE | 102 33 500 A1 | 2/2004 |
| WO | 9723466 A1 | 7/1997 |
| WO | 97/41844 A1 | 11/1997 |
| WO | 98/54156 A1 | 12/1998 |
| WO | 0038786 A2 | 7/2000 |
| WO | 0078735 A1 | 12/2000 |
| WO | 01/27081 A1 | 4/2001 |
| WO | 01/32651 A1 | 5/2001 |
| WO | 0172721 A2 | 10/2001 |

(Continued)

OTHER PUBLICATIONS

Jones, H. E. et al; "Effect of an EGF-R Selective Tyrosine Kinase Inhibitor and an Anti-Androgen on LNCaP Cells: Identification of Divergent Growth Regulatory Pathways"; The Prostate 49:38-47 (2001) XP008022176.
International Search Report for PCT/EP2004/004363 mailed on Nov. 5, 2004.
Abstract in English for DE10042696, copyright 2006.
Abstract in English for DE10233500, copyright 2006.
Abstract in English for DE19924401, 2000.
Sielecki et al., "Cyclin-Dependent Kinase Inhibitors: Useful Targets in Cell Cycle Regulation", Journal of Medicinal Chemistry, 2000, 43 (1), p. 1-18.
Bramson et al., "Oxindole-Based Inhibitors of Cyclin-Dependent Kinase 2 (CDK2): Design, Synthesis, Enzymatic Activities, and X-ray crystallographic Analysis", Journal of Medicinal Chemisty, 2001, 44 (25), p. 4339-4358.

(Continued)

Primary Examiner—James D Anderson
(74) Attorney, Agent, or Firm—Michael P. Morris; Anthony P. Bottino

(57) ABSTRACT

The present invention relates to a pharmaceutical combination for the treatment of diseases which involves cell proliferation, migration or apoptosis of myeloma cells, or angiogenesis. The invention also relates to a method for the treatment of said diseases, comprising co-administration of effective amounts of specific active compounds and/or co-treatment with radiation therapy, in a ratio which provides an additive and synergistic effect, and to the combined use of these specific compounds and/or radiotherapy for the manufacture of corresponding pharmaceutical combination preparations.

5 Claims, 3 Drawing Sheets

FOREIGN PATENT DOCUMENTS

Figure 1:
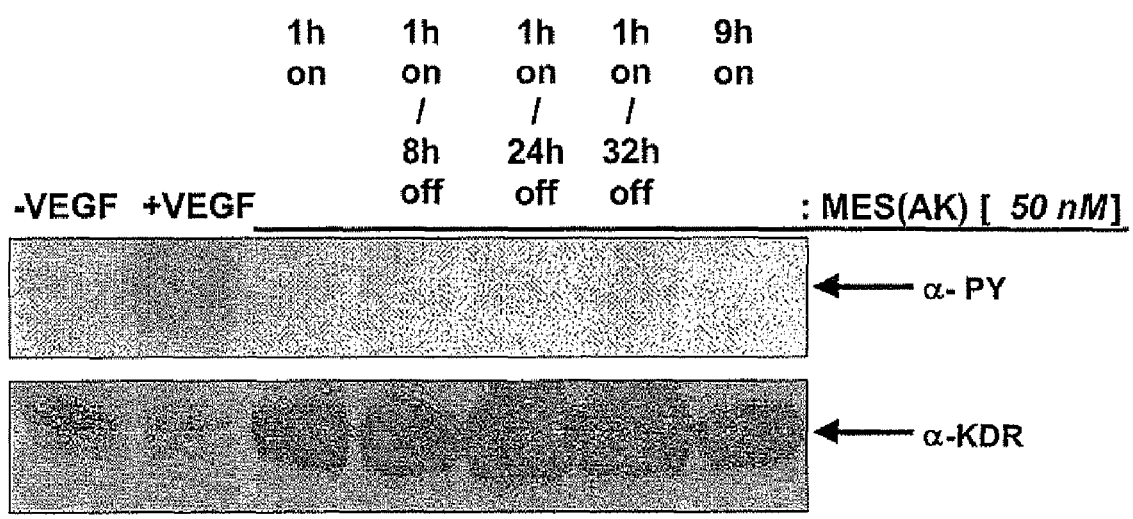

| | | |
|---|---|---|
| WO | 02/50043 A1 | 6/2002 |
| WO | 02/070008 A1 | 9/2002 |
| WO | 02092091 A1 | 11/2002 |
| WO | 03/011837 A1 | 2/2003 |
| WO | 03/022815 A1 | 3/2003 |
| WO | 03026574 A2 | 4/2003 |
| WO | 03/065995 A2 | 8/2003 |
| WO | 03094921 A2 | 11/2003 |
| WO | 2004096224 A2 | 11/2004 |
| WO | 2005037824 A2 | 4/2005 |
| WO | 2006018182 A1 | 2/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2009147218 A1 | 12/2009 |

OTHER PUBLICATIONS

Hennequin et al., "Novel 4-Anilinoquinazolines with c-7 Basic Side Chains: Design and Structure Activity Relationship of a series of Potent, Orally Active, VEGF Receptor Tyrosine Kinase Inhibitors", Journal of Medicinal Chemistry, 2002, 45 (6), p. 1300-1312.

Manley et al., "Anthranilic Acid Amides: A Novel Class of Antiangiogenic VEGF Recepto Kinase Inhibitors", Journal of Medicinal Chemistry, 2002, 45 (26), p. 5687-5693.

COMBINATIONS FOR THE TREATMENT OF DISEASES INVOLVING CELL PROLIFERATION, MIGRATION OR APOPTOSIS OF MYELOMA CELLS OR ANGIOGENESIS

APPLICATION DATA

"This application is a continuation of U.S. Ser. No. 10/830,147, filed Apr. 22, 2004, which claimed benefit of U.S. Provisional Application Ser. No. 60/542,036, filed on Feb. 5, 2004, and claims benefit to EP 03 009 587 filed Apr. 29, 2003, EP 04 000 508 filed Jan. 13, 2004 and EP 04 001 171 filed Jan. 21, 2004 the contents of all of which are hereby incorporated by reference in their entirety".

FIELD OF THE INVENTION

This invention relates to a method for the treatment of diseases involving cell proliferation, migration or apoptosis of myeloma cells, or angiogenesis, which method comprises co-administration to a person in need of such treatment and/or co-treatment of a person in need of such treatment with effective amounts of:

(i) a selected protein tyrosine kinase receptor antagonist; and (ii) at least a further chemotherapeutic or naturally occurring, semi-synthetic or synthetic therapeutic agent; and/or (iii) radiotherapy or radio-immunotherapy.

This invention relates also to suitable pharmaceutical compositions comprising effective amounts of:

(i) a selected protein tyrosine kinase receptor antagonist; and (ii) at least a further chemotherapeutic or naturally occurring, semi-synthetic or synthetic therapeutic agent;

and optionally adapted for a co-treatment with radiotherapy or radio-immunotherapy, as a combined preparation for simultaneous, separate or sequential use in the treatment of diseases involving cell proliferation, migration or apoptosis of myeloma cells, or angiogenesis, and especially for inhibiting tumour growth, survival and metastasis.

This invention relates also to the combined use of effective amounts of:

(i) a selected protein tyrosine kinase receptor antagonist; and (ii) at least a further chemotherapeutic or naturally occurring, semi-synthetic or synthetic therapeutic agent;

for the manufacture of a pharmaceutical combined preparation for simultaneous, separate or sequential use in the treatment of diseases involving cell proliferation, migration or apoptosis of myeloma cells, or angiogenesis, and especially for inhibiting tumour growth, survival and metastasis, optionally in combination with a co-treatment with radiotherapy or radio-immunotherapy.

This invention relates also to the use of an effective amount of a selected protein tyrosine kinase receptor antagonist, for the manufacture of a pharmaceutical composition adapted for a simultaneous, separate or sequential co-treatment with radiotherapy or radio-immunotherapy of diseases involving cell proliferation, migration or apoptosis of myeloma cells, or angiogenesis, and especially for inhibiting tumour growth, survival and metastasis.

BACKGROUND OF THE INVENTION

In the last decade, the biological activity of several types and sub-types of the protein tyrosin kinase receptor family have been characterised such as, for example, the epidermal growth factor receptor EGFR and its subtypes ErbB-2 and ErbB-4 (Brignola et al., Journal of Biological Chemistry, Vol. 277, No. 2, pp. 1576-1585, 2002) or the vascular endothelial growth factor receptors VEGFR 1-3 together with its ligand VEGF and its four sub-types known to date (Jung et al., European Journal of Cancer, Vol. 38, pp. 1133-1140, 2002). Similar studies reported in previous reports show that the overexpression of some of these receptors is implicated in multiple forms of cancer. For example, studies have provided evidence that the epidermal growth factor EGF acts as a growth factor in tumours, and that the vascular endothelial growth factor VEGF is one of the most common mediators of tumor angiogenesis, which is essential for the growth and metastasis of solid tumours. Inhibitors of the receptors have thus been and are still evaluated for cancer therapy (see for example the article of Cerrington et al. In Advances in Cancer Research, Academic Press 2000, pp. 1-38).

Recent studies have also suggested to combine several receptor antagonists together, or in further combination with a chemotherapeutic agent or radiation. For example, WO 02/070008 suggests the combination of an antagonist specifically directed against the VEGF receptor with an antagonist specifically directed against the EGF receptor, optionally together with radiation or a chemotherapeutic agent, for the inhibition of tumour growth. As example of suitable specific antagonists, WO 02/070008 discloses monoclonal antibodies directed against the VEGF receptor and monoclonal antibodies directed against the EGF receptor.

Thus, a large number of protein tyrosine kinase receptor antagonists are currently in clinical development for the treatment of cancer (see for example the Expert Opinion Review of Laid & Cherrington in Expert Opin. Invest. Drugs, Vol. 12, No. 1, pp. 51-64, 2003). However, proof of efficacy for these substances, used alone or with other cancer therapies, in the treatment of oncological diseases, has so far not been achieved, either because of a lack of additional benefit over the standard therapy or because of the discovery of unacceptable side-effects.

For example, it has been recently published that an angiogenesis inhibitor which has already been clinically tested, also in conjunction with chemotherapy, namely the inhibitor with code name SU5416, developed by Pharmacia for the treatment of cancer, was associated with disturbing side effect, namely thromboembolic events (Ken Garber and Ann Arbor, Nature Biotechnology, Vol. 20, pp. 1067-1068, November 2002).

For the treatment of diseases of oncological nature, a large number of chemotherapeutic agents have already been suggested, which can be used as mono-therapy (treatment with one agent) or as combination therapy (simultaneous, separate or sequential treatment with more than one agent) and/or which may be combined with radiotherapy or radio-immunotherapy. In this respect, chemotherapeutic agent means a naturally occurring, semi-synthetic or synthetic chemical compound which, alone or via further activation, for example with radiations in the case of radio-immunotherapy, inhibits or kills growing cells, and which can be used or is approved for use in the treatment of diseases of oncological nature, which are commonly also denominated as cancers. In the literature, these agents are generally classified according to their mechanism of action. In this matter, reference can be made, for example, to the classification made in "Cancer Chemotherapeutic Agents", American Chemical Society, 1995, W. O. Foye Ed.

Thus, within the meaning of the present invention, the following classes of chemotherapeutic agents are especially of interest, although not representing a limitation:

- Synthetic small molecule VEGF receptor antagonists
- Small molecule growth factor (GF) receptor antagonists
- Inhibitors of the EGF receptor and/or VEGF receptor and/or integrin receptors or any other protein tyrosine kinase receptors, which are not classified under the synthetic small-molecules
- Inhibitors directed to EGF receptor and/or VEGF receptor and/or integrin receptors or any other protein tyrosine kinase receptors, which are fusion proteins
- Compounds which interact with nucleic acids and which are classified as alkylating agents or platinum compounds
- Compounds which interact with nucleic acids and which are classified as anthracyclines, as DNA intercalators or as DNA cross-linking agents
- Anti-metabolites
- Naturally occurring, semi-synthetic or synthetic bleomycin type antibiotics (BLM-group antibiotics)
- Inhibitors of DNA transcribing enzymes, especially topoisomerase I or topoisomerase II inhibitors
- Chromatin modifying agents
- Mitosis inhibitors, anti-mitotic agents, or cell-cycle inhibitors
- Proteasome inhibitors
- Enzymes
- Hormones, hormone antagonists or hormone inhibitors, or inhibitors of steroid biosynthesis
- Steroids
- Cytokines, hypoxia-selective cytotoxins, inhibitors of cytokines, lymphokines, antibodies directed against cytokines or oral and parenteral tolerance induction strategies
- Supportive agents
- Chemical radiation sensitizers and protectors
- Photochemically activated drugs
- Synthetic poly- or oligonucleotides
- Other chemotherapeutic or naturally occurring, semi-synthetic or synthetic therapeutic agents, such as cytotoxic antibiotics, antibodies targeting surface molecules of cancer cells, inhibitors of metalloproteinases, inhibitors of oncogenes, inhibitors of gene transcription or of RNA translation or protein expression, or complexes of rare earth elements Further classes of compounds, so-far not classified as chemotherapeutic agents, which are naturally occurring, semi-synthetic or synthetic therapeutic agents, such as the non-steroidal anti-inflammatory drugs, especially the cyclooxygenase (COX) inhibitors and more specifically the COX-2 inhibitors, are also of interest for combination therapies.

Even if the concept of combining several therapeutic agents or therapies already has been suggested, and although various combination therapies are under investigation and in clinical trials, there is still a need for new and efficient therapeutic agents for the treatment of diseases in which cell proliferation, migration or apoptosis of myeloma cells, or angiogenesis, and there is still a need to develop further combinations which can show increased efficacy and reduced side-effects.

These diseases may as well be of oncological nature, which includes all types of malignant neoplasias or cancers, or of non-oncological nature, such as diabetic retinopathy, rheumatoid arthritis or psoriasis.

SUMMARY OF THE INVENTION

It has now been found that co-administration to a person in need of such treatment and/or co-treatment of a person in need of such treatment with effective amounts of (i) a selected protein tyrosine kinase receptor antagonist, and (ii) at least a further chemotherapeutic or naturally occurring, semi-synthetic or synthetic therapeutic agent, and/or (iii) radiotherapy or radioimmunotherapy, provides unexpected advantages in the treatment of diseases in which cell proliferation, migration or apoptosis of myeloma cells, or angiogenesis are involved, to a person in need of such treatment, with high efficacy, in comparison to administration of any of these substances alone and/or treatment with radiotherapy or radioimmunotherapy.

It has been further found that this co-administration or co-treatment is especially efficient if the selected protein tyrosine kinase receptor antagonist is an antagonist of at least one receptor selected from VEGFR1 to 3, PDGFRα and β, FGFR1, 2 and 3, EGFR, HER2, IGF1R, HGFR or c-Kit.

It has been further found that this co-administration or co-treatment is especially efficient if the selected protein tyrosine kinase receptor antagonist is an antagonist of at least one receptor selected from VEGFR 1 to 3, PDGFRα and β, FGFR1, 2 and 3, EGFR, HER2, IGF1R, HGFR or c-Kit, and further an antagonist of a src tyrosine kinase family member, and especially of src, lck, lyn and fyn, and/or further an antagonist of at least one complex of a cyclin dependent kinase with its specific cyclin or with a viral cyclin, such as CDK1, CDK2, CDK3, CDK4, CDK5, CDK6, CDK7, CDK8 and CDK9 with their specific cyclins A, B1, B2, C, D1, D2, D3, E, F, G1, G2, H, I and K, and/or further an inhibitor of the paracrine IL-6 secretion.

Further it has been found that the diseases which can be treated by the combination in accordance with the present invention are all kind of diseases in which cell proliferation, migration or apoptosis of myeloma cells, or angiogenesis are involved, which can be of oncological nature such as all types of malignant neoplasias or cancers, or of non-oncological nature, such as diabetic retinopathy, rheumatoid arthritis, or psoriasis.

Further it has been found that the combination treatment in accordance with the present invention is especially efficient for inhibiting tumour growth, survival and metastasis.

Further it has been found that the combination treatment in accordance with the present invention is especially efficient with selected active substances, selected dosages and selected dosage forms.

Thus, the present invention provides a method for the treatment of diseases involving cell proliferation, migration or apoptosis of myeloma cells, or angiogenesis, which method comprises simultaneous, separate or sequential co-administration of effective amounts of:

(i) an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof; and (ii) at least a further chemotherapeutic or naturally occurring, semi-synthetic or synthetic therapeutic agent;

in the form of a combined preparation, optionally adapted for a co-treatment with radiotherapy or radio-immunotherapy, to a person in need of such treatment.

The present invention provides also a method for the treatment of diseases involving cell proliferation, migration or apoptosis of myeloma cells, or angiogenesis, which method comprises a simultaneous, separate or sequential co-treatment with an effective amount of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or with a polymorph, metabolite or pharmaceutically acceptable salt thereof, and with radiotherapy or radio-immunotherapy.

The protein tyrosine kinase receptor antagonist used in the method in accordance with the present invention is preferably an antagonist of at least one receptor selected from VEGFR 1 to 3, PDGFR α and β, FGFR1, 2 and 3, EGFR, HER2, IGF1R, HGFR, c-Kit, and further an antagonist of a src-tyrosine kinase family member, and especially of src, lck, lyn or fyn.

In a further preferred embodiment, the protein tyrosine kinase receptor antagonist may further be an antagonist of at least one complex of a cyclin dependent kinase with its specific cyclin or with a viral cyclin, such as CDK1, CDK2, CDK3, CDK4, CDK5, CDK6, CDK7, CDK8 and CDK9 with their specific cyclins A, B1, B2, C, D1, D2, D3, E, F, G1, G2, H, I and K, and/or further an inhibitor of the paracrine IL-6 secretion.

In one preferred embodiment, the protein tyrosine kinase receptor antagonist is selected from specific compounds.

The further chemotherapeutic or naturally occurring, semi-synthetic or synthetic therapeutic agent used in the method in accordance with the present invention can be any available chemotherapeutic or naturally occurring, semi-synthetic or synthetic therapeutic agent, and more particularly the chemotherapeutic agents which are commonly used for the treatment of cancer. Preferred chemotherapeutic agents are selected from the following groups: synthetic small molecule VEGF receptor antagonists, small molecule growth factor (GF) receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids and which are classified as alkylating agents or platinum compounds, compounds which interact with nucleic acids and which are classified as anthracyclines, as DNA intercalators (including DNA minor-groove binding compounds) or as DNA cross-linking agents, anti-metabolites, naturally occurring, semi-synthetic or synthetic bleomycin type antibiotics (BLM-group antibiotics), inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists or hormone inhibitors, or inhibitors of steroid biosynthesis, steroids, cytokines, hypoxia-selective cytotoxins, inhibitors of cytokines, lymphokines, antibodies directed against cytokines or oral and parenteral tolerance induction strategies, supportive agents, chemical radiation sensitizers and protectors, photochemically activated drugs, synthetic poly- or oligonucleotides, optionally modified or conjugated, non-steroidal anti-inflammatory drugs, cytotoxic antibiotics, antibodies targeting surface molecules of cancer cells, inhibitors of metalloproteinases, metals, inhibitors of oncogenes, inhibitors of gene transcription or of RNA translation or protein expression, complexes of rare earth elements, or photochemotherapeutic agents.

In one preferred embodiment, amongst the chemotherapeutic or naturally occurring, semi-synthetic or synthetic therapeutic agents, specific compounds are preferred.

In one embodiment, the disease treated in the method in accordance with the present invention is preferably an oncological disease. In a preferred embodiment, the disease is selected from solid tumours, such as urogenital cancers (such as prostate cancer, renal cell cancers, bladder cancers), gynecological cancers (such as ovarian cancers, cervical cancers, endometrial cancers), lung cancer, gastrointestinal cancers (such as colorectal cancers, pancreatic cancer, gastric cancer, oesophageal cancers, hepatocellular cancers, cholangiocellular cancers), head and neck cancer, malignant mesothelioma, breast cancer, malignant melanoma or bone and soft tissue sarcomas, and haematologic neoplasias, such as multiple myeloma, acute myelogenous leukemia, chronic myelogenous leukemia, myelodysplastic syndrome and acute lymphoblastic leukemia. In a preferred embodiment, the disease is hormone sensitive or hormone refractory prostate cancer, ovarian carcinoma, or small cell lung cancer.

In another embodiment, the disease treated in the method in accordance with the present invention is preferably a non-oncological disease selected from diabetic retinopathy, rheumatoid arthritis or psoriasis.

Thus, the beneficial efficacy of the methods in accordance with the invention are mainly based on the additive and synergistic effects of the combined treatment, or to an improved tolerability of the treatment by the patient due, for example, to the administration of lower doses of the therapeutic agents involved.

The unexpected advantages mentioned above may also be due to a more efficient apoptosis induction by the chemotherapeutic agent, once the constitutively active survival signal of the protein tyrosin kinase receptor, mediated by the tumour, is inhibited by the selected protein tyrosine kinase receptor antagonist.

In the case of the use of an antagonist of protein tyrosine kinase receptors or an inhibitor of other mediators involved in angiogenesis, such as for example the vascular endothelial growth factors (VEGF), the vascular permeability factors, the basic fibroblast growth factor (bFGF), interleukin-6 (IL-6) or interleukin-8 (IL-8), the epidermal growth factor (EGF) or the platelet-derived growth factor (PDGF), one of the advantages of the method and composition in accordance with the present invention lies in a targeting of the treatment to tumour-associated vasculature rather than, or together with, the tumour itself, in order to cut the energy supply of cancerous cells.

A further advantage is that an induction or reinstatement of the sensitivity towards the chemotherapeutic agent is expected in patients treated with the combination of chemotherapeutic agents for which the sensitivity gets lost in the course of the treatment and of a VEGFR antagonist. This is especially the case of patients suffering from refractory multiple myeloma and treated with steroids as chemotherapeutic agent. A combination treatment with steroids and a VEGFR antagonist is expected to restore the steroid sensitivity of patients suffering from refractory multiple myeloma.

According to the present invention, a synergistic combined preparation is meant to comprise an amount of the selected protein tyrosine kinase receptor antagonist, or of a polymorph, metabolite or pharmaceutically acceptable salt of this active compound, and an amount of the further chemotherapeutic or naturally occurring, semi-synthetic or synthetic therapeutic agent, and/or radiotherapy or radio-immunotherapy, wherein the amount of the individual therapeutic agents alone is insufficient to achieve the therapeutic effect achieved by the administration of the combination of said therapeutic agents, and wherein the combined effects of the amounts of the therapeutic agents is greater than the sum of the therapeutic effects achievable with the amounts of the individual therapeutic agents.

Viewed from a different aspect, the present invention also relates to a pharmaceutical combination for the treatment of diseases in which cell proliferation, migration or apoptosis of myeloma cells, or angiogenesis are involved, comprising a selected specific protein tyrosine kinase receptor antagonist and a further chemotherapeutic or naturally occurring, semi-synthetic or synthetic therapeutic agent, and/or radiotherapy or radio-immunotherapy, as a combined preparation for simultaneous, separate or sequential use in treatment of said diseases, optionally together with one or more pharmaceutically acceptable diluents and/or carriers.

Viewed from a different aspect, the present invention also relates to a pharmaceutical combination preparation kit for the treatment of diseases involving cell proliferation, migration or apoptosis of myeloma cells, or angiogenesis, comprising a therapeutically effective amount of a selected protein tyrosine kinase receptor antagonist, or of a polymorph, metabolite or pharmaceutically acceptable salt thereof, and a therapeutically effective amount of a further chemotherapeutic or naturally occurring, semi-synthetic or synthetic therapeutic agent, characterised in that the protein tyrosine kinase receptor antagonist is comprised within a first compartment and the further chemotherapeutic or naturally occurring, semi-synthetic or synthetic therapeutic agent is comprised within a second compartment, such that the administration to a patient in need thereof can be simultaneous, separate or sequential, said combination preparation kit being optionally further adapted for a co-treatment with radiotherapy or radio-immunotherapy.

In one embodiment in accordance with the present invention, in each compartment of the pharmaceutical combination preparation kit, each active substance is formulated for an oral administration.

Viewed from a further aspect, the present invention thus also provides the use of a selected protein tyrosine kinase receptor antagonist in combination with a further chemotherapeutic or naturally occurring, semi-synthetic or synthetic therapeutic agent, and/or adapted for a co-treatment with radiotherapy or radio-immunotherapy, for the manufacture of a pharmaceutical combination preparation for the treatment of the diseases or indications mentioned hereinbefore.

Within the meaning of the present invention, effective amounts of therapeutic agents and/or of a therapeutic treatment by radiotherapy or radio-immunotherapy means amounts of the agents and/or of the treatment by radiotherapy or radio-immunotherapy which are effective to achieve a therapeutic effect when used in combination.

DETAILED DESCRIPTION OF THE INVENTION

The Diseases

As already mentioned hereinbefore, the diseases which can be treated by the combination in accordance with the present invention are all kind of diseases in which cell proliferation, migration or apoptosis of myeloma cells, or angiogenesis are involved, which can be of oncological nature such as all types of malignant neoplasias or cancers, or of non-oncological nature, such as diabetic retinopathy, rheumatoid arthritis, or psoriasis. Among cancers, selected specific target indications are solid tumours, such as urogenital cancers (such as prostate cancer, renal cell cancers, bladder cancers), gynecological cancers (such as ovarian cancers, cervical cancers, endometrial cancers), lung cancer, gastrointestinal cancers (such as colorectal cancers, pancreatic cancer, gastric cancer, oesophageal cancers, hepatocellular cancers, cholangiocellular cancers), head and neck cancer, malignant mesothelioma, breast cancer, malignant melanoma or bone and soft tissue sarcomas, and haematologic neoplasias, such as multiple myeloma, acute myelogenous leukemia, chronic myelogenous leukemia, myelodysplastic syndrome and acute lymphoblastic leukemia.

The combination treatment in accordance with the present invention is especially efficient for inhibiting tumour growth, survival and metastasis.

Of special interest for the combination treatment is the treatment of hormone sensitive or hormone refractory prostate cancer, ovarian carcinoma, non small cell lung cancer, small cell lung cancer, or multiple myeloma.

The Selected Protein Tyrosine Kinase Receptor Antagonist

As already mentioned hereinbefore, the selected protein tyrosine kinase receptor antagonists that can be used in the context of the present invention include all substances that inhibit the stimulation or activation of a protein tyrosine kinase receptor by a protein tyrosine kinase receptor ligand. In the case of a protein tyrosine kinase receptor belonging to the family of the growth factor receptors, such inhibition of stimulation or activation inhibits the growth of cells that express the receptor.

Some examples of growth factor receptors involved in tumorigenesis are the receptors for epidermal growth factor (EGFR), vascular endothelial growth factors (VEGFRs), platelet-derived growth factor (PDGFR), insulin-like growth factor (IGFR), nerve growth factor (NGFR), and fibroblast growth factor (FGFR).

By inhibition of stimulation or activation of protein tyrosine kinase receptor is meant any decrease in the activation of the receptor, which need not completely prevent or stop activation of the receptor.

Moreover, inhibition of the receptor stimulation or activation, as defined by the present invention, means inhibition resulting from interaction of the antagonist and the receptor or its ligand. By interaction is meant sufficient physical or chemical interaction between the antagonist and the receptor, such that protein tyrosin kinase activity is inhibited. One of skill in the art would appreciate that examples of such chemical interactions, which include association or bonding, are known in the art and include covalent bonding, ionic bonding, hydrogen bonding, etc . . . , between the antagonist and the receptor or its ligand.

Increased protein tyrosine kinase receptor stimulation or activation can result from higher levels of ligand, receptor gene amplification, increased transcription of the receptor or mutations that cause unregulated receptor signalling. Amplification of the gene encoding the receptor results in an increased number of ligands binding to the receptor, which can further stimulate cell proliferation. The protein tyrosine kinase receptor may also be over-expressed in the absence of gene amplification, presumably through mutations that increase its transcription, mRNA translation, or stability of the protein. Protein tyrosine kinase receptor mutants of the EGFR type have already been identified in gliomas, non-small cell lung carcinomas, ovarian carcinomas and prostate carcinomas, that have a constitutively active protein tyrosin kinase, suggesting a role for high-level EGFR activity rather than EGFR over-expression in these cancers (see for example Pedersen et al., Ann. Oncol., Vol. 12 (6), pp. 745-60, 2001).

In one embodiment in accordance with the present invention, the selected protein tyrosine kinase receptor antagonist inhibits the binding of the protein tyrosine kinase receptor to its ligand.

Binding of a ligand to an external, extracellular domain of the receptor stimulates receptor dimerization, autophosphorylation of the receptor, activation of the receptor's internal, cytoplasmic protein tyrosin kinase domain, and initiation of multiple signal transduction pathways involved in regulation of DNA synthesis, cell division, vasculogenesis or angiogenesis. The inhibition produced by the presence of the antagonist will consequently reduce this stimulation.

In another embodiment in accordance with the present invention, the selected protein tyrosine kinase receptor antagonist binds directly to the receptor. The antagonist can bind externally to the extra-cellular portion of the receptor, which may or may not inhibit binding of the ligand, or internally to the protein tyrosine kinase domain. Examples of such antagonists include, without limitation, biological molecules, such as antibodies (and functional equivalents thereof) specific for the receptor, and synthetic kinase inhibitors that act directly on the cytoplasmic domain of the receptor, such as the so-called "small molecule tyrosine kinase inhibitors". A non-exhaustive list of small molecule tyrosine kinase inhibitors can be found in the review article of Laid & Cherrington, Expert Opinion Invest. Drugs, Vol. 12, No. 1, 2003, the content of which is incorporated herein by reference.

Additional protein tyrosine kinase receptor antagonists can easily be determined using well-known methods. The selected receptor antagonists to be used in the present invention inhibit the protein tyrosin kinase activity of the receptor, which generally involves phosphorylation events. Accordingly, phosphorylation assays may for example be useful in determining antagonists useful in the context of the present invention. In addition, methods specific for detection of the receptor expression can be utilized. These include immunohistochemistry for detection of protein expression, fluorescence in situ hybridization for detection of gene amplification, competitive radioligand binding assays, solid matrix blotting techniques, such as Northern and Southern blots, reverse transcriptase polymerase chain reaction and ELISA.

In accordance with the present invention, the selected protein tyrosine kinase receptor antagonist is preferably an antagonist of at least one receptor selected from VEGFR 1 to 3, PDGFR α and β, FGFR1, 2 and 3, EGFR, HER2, IGF1R, HGFR, c-Kit, and further an antagonist of one of the src-tyrosine kinase family members, and especially src, lck, lyn or fyn, or a polymorph, metabolite or pharmaceutically acceptable salt thereof. The selected protein tyrosine kinase receptor antagonist may further be an antagonist of at least one complex of a cyclin dependent kinase with its specific cyclin or with a viral cyclin, such as CDK1, CDK2, CDK3, CDK4, CDK5, CDK6, CDK7, CDK8 and CDK9 with their specific cyclins A, B1, B2, C, D1, D2, D3, E, F, G1, G2, H, I and K, and/or further an inhibitor of the paracrine IL-6 secretion.

In a further embodiment in accordance with the present invention, the combination of the active substances is intended for the treatment of oncological diseases involving angiogenesis.

Tumour angiogenesis plays an important role in the progression of human malignancies. Inhibition of this process is thought to be an excellent point of therapeutic intervention in the treatment of cancer. Signal transduction through the vascular endothelial growth factor receptor 2 (VEGFR-2) has been shown to play a pivotal role in the proliferation, survival and migration of endothelial cells in tumour angiogenesis.

In this matter, potent and orally available low molecular weight antagonists of VEGFR-2 have been developed as new compounds which are useful for the treatment of diseases involving cell proliferation, migration or apoptosis of myeloma cells, or angiogenesis, and especially as new cancer therapeutic agents. These antagonists are thus inhibitors of the activity of the receptor. Some of these antagonists are also antagonists of further growth factor receptors, such as VEGFR-3, PDGFR α and β, FGFR1, 2 and 3, EGFR, HER2, IGF1R, HGFR, c-Kit, and some also antagonists of the src-tyrosine kinase family members src, lck, lyn and fyn.

These compounds are disclosed in WO 02/36564, WO 99/52869, WO 00/18734, WO 00/73297, WO 01/27080, WO 01/27081 and WO 01/32651 The cited documents are herewith incorporated by reference with respect to any aspects disclosed relating to these specific compounds.

The following compounds are particularly representative and are all combined inhibitors of VEGFR-2 and lck which may be used as the selected protein tyrosine kinase receptor antagonist within the meaning of the present invention.

(A) (Z)-3-(1-(4-(N-(2-dimethylamino-ethyl)-N-methylsulfonyl-amino)-phenylamino)-1-phenyl-methylene)-2-indolinone;

(B) (Z)-3-(1-(4-(N-(3-dimethylaminopropyl)-N-propionyl-amino)-phenylamino)-1-phenyl-methylene)-2-indolinone;

(C) (Z)-3-(1-(4-(dimethylaminomethyl)-phenylamino)-1-phenyl-methylene)-5-(butylcarbamoyl)-2-indolinone;

(D) (Z)-3-(1-(4-(dimethylaminomethyl)-phenylamino)-1-phenyl-methylen)-5-(cyclohexylmethyl-carbamoyl)-2-indolinone;

(E) (Z)-3-(1-(4-(N-methylsulfonyl-N-(2-dimethylamino-ethyl)-amino)-phenylamino)-1-phenyl-methylen)-5-(cyclohexylmethyl-carbamoyl)-2-indolinone;

(F) (Z)-3-(1-(4-(butylaminomethyl)-phenylamino)-1-phenyl-methylen)-5-(cyclohexylmethyl-carbamoyl)-2-indolinone;

(G) (Z)-3-(1-(4-(pyrrolidin-1-yl-methyl)-phenylamino)-1-phenyl-methylen)-5-(cyclohexylmethyl-carbamoyl)-2-indolinone;

(H) (Z)-3-(1-(4-(diethylaminomethyl)-phenylamino)-1-phenyl-methylen)-5-(cyclohexylmethyl-carbamoyl)-2-indolinone;

(I) (Z)-3-(1-(4-(diethylaminomethyl)-phenylamino)-1-phenyl-methylen)-5-(N-(3-chlorobenzyl)-carbamoyl)-2-indolinone;

(J) (Z)-3-(1-(4-(diethanolaminomethyl)-phenylamino)-1-phenyl-methylen)-5-(butylcarbamoyl)-2-indolinone;

(K) (Z)-3-(1-(4-(dimethylaminomethyl)-phenylamino)-1-phenyl-methylen)-5-(N-(3-chlorobenzyl)-carbamoyl)-2-indolinone;

(L) (Z)-3-(1-(4-(N-acetyl-N-(2-dimethylamino-ethyl)-amino)-phenylamino)-1-phenyl-methylen)-5-(N-(3-chlorobenzyl)-carbamoyl)-2-indolinone;

(M) (Z)-3-(1-(4-(butylaminomethyl)-phenylamino)-1-phenyl-methylen)-5-(N-(3-chlorobenzyl)-carbamoyl)-2-indolinone;

(N) (Z)-3-(1-(4-(dimethylaminomethyl)-phenylamino)-1-phenyl-methylene)-6-methoxycarbonyl-2-indolinone;

(O) (Z)-3-(1-(4-(N-(3-dimethylamino-propyl)-N-acetyl-amino)-phenylamino)-1-phenyl-methylene)-6-methoxycarbonyl-2-indolinone;

(P) (Z)-3-(1-(4-(ethylaminomethyl)-phenylamino)-1-phenyl-methylene)-6-methoxycarbonyl-2-indolinone;

(Q) (Z)-3-(1-(4-(1-methyl-imidazol-2-yl)-phenylamino)-1-phenyl-methylene)-6-methoxycarbonyl-2-indolinone;

(R) (Z)-3-(1-(4-(N-(dimethylaminomethylcarbonyl)-N-methyl-amino)-phenylamino)-1-phenyl-methylene)-6-methoxycarbonyl-2-indolinone;
(S) (Z)-3-(1-(4-(methylaminomethyl)-anilino)-1-phenyl-methylene)-6-methoxycarbonyl-2-indolinone;
(T) (Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone; and
(U) 4-(4-bromo-2-fluoroanilino)-6-methoxy-7-(1-methylpiperidin-4-ylmethoxy)-quinazoline, as well as their polymorphs, metabolites or pharmaceutically acceptable salts.

Compounds (A) to (B) are described in WO 00/18734, compounds (C) to (M) are described in WO 00/73297, compounds (N) to (T) are described in WO 01/27081, compound (U) is described in WO 01/32651.

Especially representative is the potent and orally available low molecular weight antagonist of VEGFR 1 to 3, PDGFRα and β, FGFR1, 2 and 3, EGFR, HER2, IGF1R, HGFR and c-Kit, which is further an antagonist of the src tyrosine kinase family members, and especially of src, lck, lyn and fyn, further an antagonist of the complex of cyclin dependent kinases with their specific cyclins or with a viral cyclin, and further an inhibitor of the paracrine IL-6 secretion, disclosed, for example, in WO 01/27081, as exemplified compound number 473, as well as its polymorphs, metabolites or pharmaceutically acceptable salts. This compound, referred to as (T) in the above list, is 3-Z-[1-(4-(N-((4-methyl-piperazin-1-yl)-methylcarbonyl)-N-methyl-amino)-anilino)-1-phenyl-methylene]-6-methoxycarbonyl-2-indolinone.

When compared to the other above exemplified compounds, this compound is further particularly preferred due to its high potency as inhibitor and its better toxicologic profile.

Particularly preferred is the monoethanesulfonate salt of this compound, namely the monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone, disclosed for example in unpublished German patent application DE 102 33 500.1, unpublished PCT/03/07822 and unpublished U.S. patent application Ser. No. 10/623,971.

In accordance with what is disclosed in DE 102 33 500.1, unpublished PCT/03/07822 and unpublished U.S. patent application Ser. No. 10/623,971, the monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone has the following chemical structure:

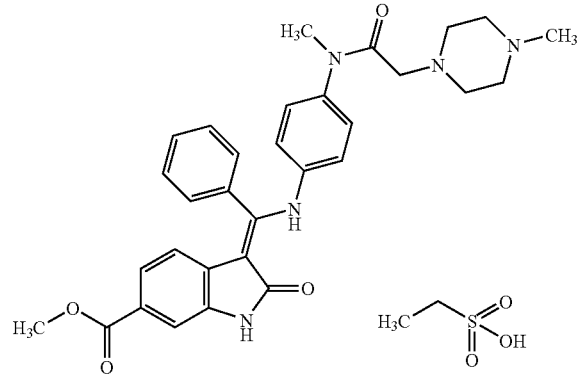

Compound MES(T)
(Monoethanesulfonate salt of compound (T))

This compound may be selectively obtained by a suitable choice of manufacturing conditions, preferably in its crystalline hemihydrate form.

This compound is characterised by a melting point of $T=305\pm5°$ C. (determined by DSC=Differential Scanning Calorimetry, using a Mettler-Toledo DSC82 apparatus; heating rate: 10 K/min).

For the manufacture of the monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone, a procedure in accordance with the following may be used.

The starting material used to prepare the monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone may be the free base 3-Z-[1-(4-(N-((4-methyl-piperazin-1-yl)-methylcarbonyl)-N-methyl-amino)-anilino)-1-phenyl-methylene]-6-methoxycarbonyl-2-indolinone, which may be obtained in accordance with a method known from the prior art and described, for example, in WO 01/27081.

Thus, in a first step and in accordance with what is described in WO 01/27081, 3-Z-[1-(4-(N-((4-methyl-piperazin-1-yl)-methylcarbonyl)-N-methyl-amino)-anilino)-1-phenyl-methylene]-6-methoxycarbonyl-2-indolinone is prepared as follows.

10.5 g (30.0 mmol) 1-acetyl-3-(1-ethoxy-1-phenylmethylene)-6-methoxycarbonyl-2-indolinone (prepared as described in WO 01/27081) and 8.60 g (33.0 mmol) N-[(4-methyl-piperazin-1-yl)-methylcarbonyl]-N-methyl-p-phenylendiamine (prepared as described in WO 01/27081) are dissolved in 80 ml dimethylformamide and mixed for 1 hour at 80° C. After cooling, 6.50 ml piperidine is added and the whole is further mixed for 2 hours at room temperature. Water is added, the liquid over the resulting precipitate is sucked up, and the precipitate is washed again with a low quantity of water. The residue is suspended in 200 ml methanol, the liquid is sucked up, and the remaining residue washed with cold water and diethylether. The resulting product is vacuum dried at 110° C.

| | |
|---|---|
| Recovered product: | 12.4 g (77% of theoretical value) |
| IR-spectroscopy: | 1610, 1655, 1711 cm$^{-1}$ |
| $T_{Smp.}$ = | 253° C. |
| Molecular formula: | $C_{31}H_{33}N_5O_4$ |
| Electrospray-mass spectrometry: | m/z = 540 [M + H]$^+$ |
| Element analysis: | |
| calculated | C 68.99 H 6.16 N 12.98 |
| found | C 68.32 H 6.29 N 12.85 |

In a second step, and in accordance with what is disclosed in DE 102 33 500.1, the monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone will be obtained as follows.

605 g (1.12 mol) 3-Z-[1-(4-(N-((4-methyl-piperazin-1-yl)-methylcarbonyl)-N-methyl-amino)-anilino)-1-phenyl-methylene]-6-methoxycarbonyl-2-indolinone are suspended in 9 liters methanol and heated to 50° C. 183.7 g (1.121 mol) of a 70% aqueous solution of ethanesulfonate is added. The resulting solution is cooled to 40° C. and mixed with 4.5 liters ter-butylmethylether. Cristallisation occurs after a few minutes. In order to achieve a complete precipitation, the whole is mixed for 16 hours at room temperature. After cooling to a temperature of 10° C., the liquid is sucked up, the precipitate is washed with 2 liters ter-butylmethylether and vacuum dried at 40° C.

| | |
|---|---|
| Recovered product: | 638 g (87.6% of theoretical value) |
| $T_{Smp.}$ = | 305 ± 5° C. (DSC 10K/min) |
| Purity (measured by HPLC): | 99.4% |
| Water content: | 1.0 bis 2.0% (KF) |

The monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone can be very easily dissolved in physiologically acceptable solubilization agents.

Additionally, the compound MES(T) is orally bioavailable in mice.

The monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone inhibits the human VEGFR-2 kinase (huVEGFR-2) with an $IC_{50}$ of 21 nM, the murine VEGFR-2 kinase (huVEGFR-2) with an $IC_{50}$ of 13 nM, and the proliferation of VEGF stimulated endothelial cells (HUVEC: $IC_{50}$=9 nM, HSMEC: $IC_{50}$=12 nM).

Furthermore, FGFR-1 and PDGFRα, two members of the split kinase domain family of receptors important in angiogenic signaling, are additionally inhibited by this compound with $IC_{50}$'s of 69 nM and 59 nM respectively.

The compound MES(T) is thus highly selective when tested against a panel of numerous different kinases, as shown in the following Table I.

TABLE I

| Kinase | $IC_{50}$ [nM] |
|---|---|
| huVEGFR-2 | 21 |
| muVEGFR-2 | 13 |
| VEGFR-3 | 13 |
| InsR | >4000 |
| IGF1R | >1000 |
| EGFR | >50000 |
| HER2 | >50000 |
| FGFR1 | 69 |
| FGFR3 | 137 |
| PDGFRα | 59 |
| CDK1 | >10000 |
| CDK2 | >10000 |
| CDK4 | >10000 |
| Lck | 16 |
| Lyn | 195 |
| Src | 156 |

Noteworthy is also that this specific antagonist shows a long lasting inhibition of the receptor VEGFR-2. On the molecular and cellular level a short exposure of the compound MES(T) to cells (e.g. endothelial cells) is enough to inhibit the activation of the receptor kinase itself and downstream signalling molecules (e.g. the MAP kinase, MAPK) as well as cellular proliferation for at least 32 h.

The results of the following experiment evidences this long-lasting inhibition effect. In order to determine the duration of the inhibition induced by MES(T) on the receptor, washout experiments were performed. HUVEC and NIH 3T3 KDR cells were exposed to MES(T) for a limited period of time, MES(T) was washed away and cell proliferation (HUVEC) or VEGFR-2 activation/phosphorylation was analysed after various periods of time. As shown in FIG. 1, the autophosphorylation of VEGFR-2 is blocked for at least 32 h after a 1 hour exposure with 50 nM MES(T). After 8 h, 24 h, and 32 h without MES(T), the cells were again stimulated with VEGF and the receptor activation was analysed. Even after 32 h no receptor activation could be observed. This strongly suggests that MES(T) exhibits sustained effects on the receptor kinase even when the MES(T) plasma concentration are very low.

Figure 2:
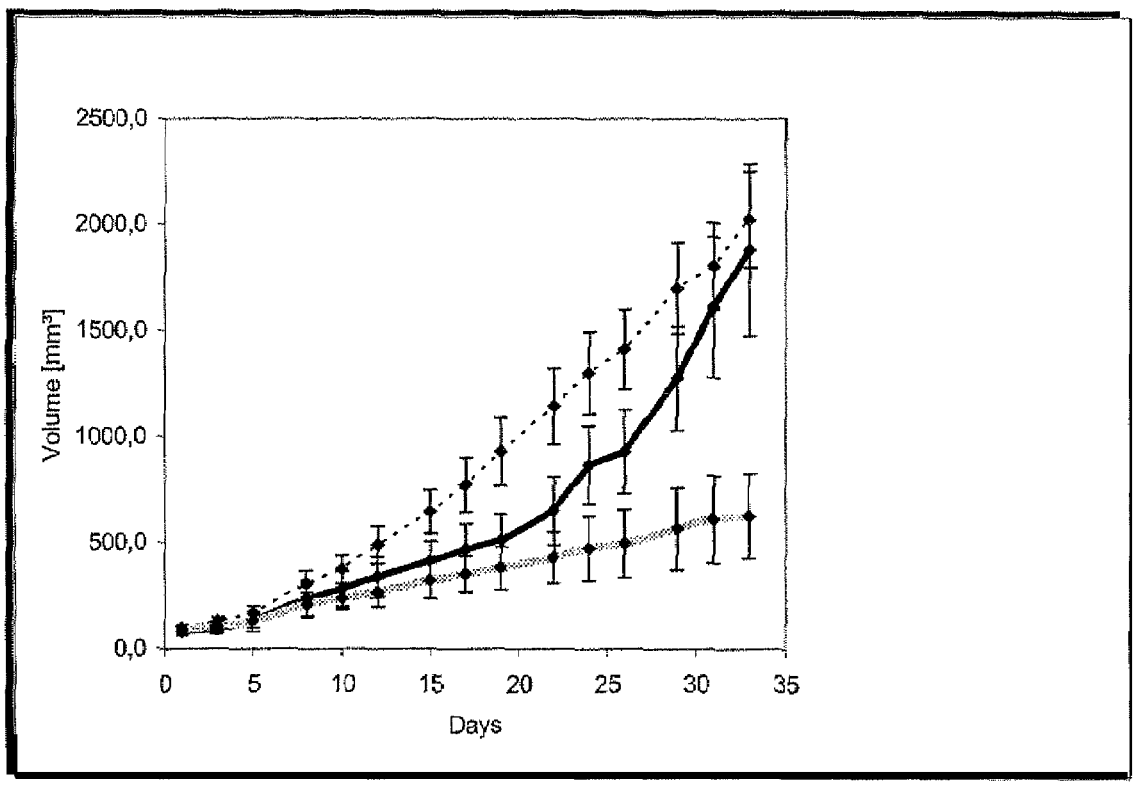

The results of the following in vivo xenograft experiment evidences the effect on tumour cells of compound MES(T). In order to determine this effect, nude mice bearing subcutaneous FaDu tumours (FaDu tumours are constituted of human squamous carcinoma cells) were orally treated with the compound MES(T). As shown in FIG. 2, when the mice were treated twice weekly with a dose of 100 mg/kg, a reduction of tumour growth with a T/C (Tumour/Control) value of 31% can be seen. By increasing the dose to 200 mg/kg orally twice weekly an even better anti-tumour effect is expected.

This indicates that this antagonist is particularly suitable for a sequential co-administration and/or co-treatment with another chemotherapeutic or naturally occurring, semi-synthetic or synthetic therapeutic agent, and/or radiotherapy or radio-immunotherapy. The scheduled treatment regimen with this antagonist may be, for example, an alternate treatment one day on/one day off, one day on/two days off, one week on/one week off, or even two weeks on/two weeks off.

The monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone is thus clearly a potent and orally available VEGFR-2 kinase inhibitor and anti-tumour agent.

With regard to all aspects of the invention, suitable selected protein tyrosine kinase receptor antagonists are also the active in vivo metabolites of the selected protein tyrosine kinase receptor antagonists. For example, an active in vivo metabolite of the protein tyrosine kinase receptor antagonist 3-Z-[1-(4-(N-((4-methyl-piperazin-1-yl)-methylcarbonyl)-N-methyl-amino)-anilino)-1-phenyl-methylene]-6-methoxycarbonyl-2-indolinone may be the unesterified compound 3-Z-[1-(4-(N-((4-methyl-piperazin-1-yl)-methylcarbonyl)-N-methyl-amino)-anilino)-1-phenyl-methylene]-6-carbonyl-2-indolinone.

Within the meaning of the present invention, all the above-exemplified compounds, and especially the compound (T) and its monoethanesulfonate salt MES(T), may also be used as mono-therapy for the treatment of the above-mentioned diseases, namely all kind of diseases in which cell proliferation, migration or apoptosis of myeloma cells, or angiogenesis are involved, which can be of oncological nature such as all types of malignant neoplasias or cancers, or of non-oncological nature, such as diabetic retinopathy, rheumatoid arthritis, or psoriasis. Among cancers, selected specific target indications for a mono-therapeutic treatment are solid tumours, such as urogenital cancers (such as prostate cancer, renal cell cancers, bladder cancers), gynecological cancers (such as ovarian cancers, cervical cancers, endometrial cancers), lung cancer, gastrointestinal cancers (such as colorectal cancers, pancreatic cancer, gastric cancer, oesophageal cancers, hepatocellular cancers, cholangiocellular cancers), head and neck cancer, malignant mesothelioma, breast cancer, malignant melanoma or bone and soft tissue sarcomas, and haematologic neoplasias, such as multiple myeloma, acute myelogenous leukemia, chronic myelogenous leukemia, myelodysplastic syndrome and acute lymphoblastic leukemia. Of special interest is the treatment of hormone sensitive or hormone refractory prostate cancer, ovarian carcinoma, non small cell lung cancer, small cell lung cancer, or multiple myeloma. The above-exemplified compounds are especially efficient for inhibiting tumour growth, survival and metastasis.

The Further Chemotherapeutic or Naturally Occurring, Semi-Synthetic or Synthetic Therapeutic Agent This compound may preferably be selected from the following classes and examples of compounds, although this list is not to be considered as limitative.

➢Synthetic Small Molecule VEGF Receptor Antagonists

Synthetic small molecule VEGF receptor antagonists of particular interest are the antagonists of the VEGF receptor of type 2, which are as well antagonists of the basic fibroblast growth factor (bFGF) and of the platelet derived growth factor (PDGF) receptors. Representative compounds are, for example, indolinone derivatives, such as those described in WO 02/36564, WO 99/52869, WO 00/18734, WO 00/73297, WO 01/27080, WO 01/27081 and WO 01/32651. Further representative small molecule VEGF receptor antagonists are the compounds described in WO 01/60814, WO 99/48868, WO 98/35958, and especially the compounds vatalanib (PTK-787/ZK222584), SU-5416, SU-6668, SU-11248, SU-14813, AZD-6474, AZD-2171, CP-547632, CEP-7055, AG-013736, IM-842 (a dipeptide of L-Glutamyl and L-Tryptophan) or GW-786034.

➢Small Molecule Growth Factor (GF) Receptor Antagonists

Small molecule growth factor (GF) receptor antagonists of particular interest are the antagonists of the protein tyrosin kinase (PTK) receptors, especially the antagonists of the epidermal growth factor (EGF) receptor, the dual antagonists of the epidermal growth factor (EGF) and of the human epidermal growth factor of type 2 (HE type 2) receptors or the antagonists of the mitogen-activated protein kinase (MAPK). Representative compounds which are dual EGFR and HER-2 antagonists are, for example, the quinazoline derivatives disclosed in WO 00/78735 and WO 02/50043, gefitinib, erlotinib, CI-1033 and GW-2016. Representative compounds which are only EGFR antagonists are, for example, iressa (ZD-1839), tarceva (OSI-774), PKI-166, EKB-569, HKI-272 and herceptin. Representative compounds which are antagonists of the mitogen-activated protein kinase (MAPK) are BAY-43-9006 (a Raf protein kinase family inhibitor) and BAY-57-9006 (a Kdr tyrosine kinase inhibitor).

A preferred compound in this class is the quinazoline derivative disclosed in WO 02/50043 as exemplified compound of Example 1(10), namely 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, or the tautomers, the stereoisomers and the salts thereof, particularly the physiologically acceptable salts thereof with inorganic or organic acids or bases. Most preferred is the di-maleic acid salt of this compound, which can easily be obtained in accordance with the following procedure. 6.0 kg (12.35 mol) of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline are heated up to 70° C. in 84 liter of ethanol. A solution of 2.94 kg (25.31 mol) maleic acid in 36 liter ethanol is added. At the beginning of crystallisation, the reaction mixture is cooled to 20° C. and stirred for 2 hours. The reaction mixture is cooled to 0° C. and stirred for 3 hours. The precipitate is suction filtered. The filter cake is washed with 19 liter of ethanol and vacuum-dried at 40° C.

A further preferred compound in this class is the 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or the salts thereof. The chemical structural formula of this compound is

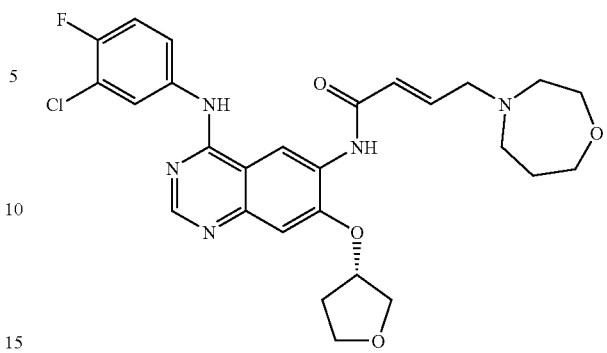

This compound may be obtained in three steps using the following manufacturing conditions.

Preparation of the Starting Compound I

4-[(3-chloro-4-fluoro-phenyl)amino]-6-[(diethoxy-phosphoryl)-acetylamino]-7-[(S)-(tetrahydrofuran-3-yl)oxy]-quinazoline 60.07 g of diethoxyphosphorylacetic acid are placed in 750 ml of N,N-dimethylformamide and at ambient temperature combined with 48.67 g of N,N'-carbonyldiimidazole. After the development of gas has ceased 90.00 g of 4-[(3-chloro-4-fluoro-phenyl)amino]-6-amino-[(S)-(tetrahydrofuran-3-yl)oxy]-quinazoline are added and the reaction mixture is stirred for about 4-5 hours at ambient temperature until the reaction is complete. The reaction mixture is then heated gently in the water bath and 750 ml of water are added twice. The thick suspension is stirred overnight and the next morning another 350 ml of water are added. The suspension is cooled in the ice bath, stirred for one hour and suction filtered. The filter cake is washed again with 240 ml of N,N-dimethylformamide/water (1:2) and 240 ml of diisopropylether and dried at 40° C. in the circulating air dryer.

Yield: 117.30 g of (88% of theory)

$R_f$-value: 0.37 (silica gel, methylene chloride/methanol=9:1)

Mass spectrum (ESI$^+$): m/z=553, 555 [M+H]$^+$

Preparation of the Starting Compound II

Homomorpholin-4-yl-acetaldehyde-hydrochloride

Prepared by stirring (2.5 hours) 4-(2,2-dimethoxy-ethyl)-homomorpholine with semi-concentrated hydrochloric acid at 80° C. The solution obtained is further reacted directly as below-described.

Preparation of the Final Compound

4-[(3-chloro-4-fluoro-phenyl)amino]-6-{[4-(homo-morpholin-4-yl)-1-oxo-2-buten-1-yl]amino}-7-[(S)-(tetrahydrofuran-3-yl)oxy]-quinazoline A solution of 3.9 g of 4-[(3-chloro-4-fluoro-phenyl)amino]-6-[2-(diethoxy-phosphoryl)-acetylamino]-7-[(S)-(tetrahydrofuran-3-yl)oxy]-quinazoline (starting compound I) in 20 ml of tetrahydrofuran is added to a solution of 300 mg of lithium chloride in 20 ml of water at ambient temperature. Then 2.35 g of potassium hydroxide flakes are added and the reaction mixture is cooled to −3° C. in an ice/acetone cooling bath. The solution of the above-obtained homomorpholin-4-yl-acetaldehyde hydrochloride (staring compound II) is then added drop wise within 5 min at a temperature of 0° C. After the addition has ended the reaction mixture is stirred for another 10 min at 0° C. and for a further hour at ambient temperature. For working up 100 ml of ethyl acetate are added and the aqueous phase is separated off. The organic phase is washed with saturated sodium chloride solution, dried over magnesium sulphate and evaporated down. The crude product is purified by chromatography over a silica gel column using ethyl acetate/methanol/conc. methanolic ammonia as eluant. The product obtained is stirred with a little di-isopropyl ether, suction filtered and dried.

Yield: 2.40 g of (63% of theory)

$R_f$ value: 0.09 (silica gel, ethyl acetate/methanol/conc. aqueous ammonia=90:10:1)

Mass spectrum (ESI$^+$): m/z=542, 544 [M+H]$^+$

➢Inhibitors of the EGF Receptor and/or VEGF Receptor and/or Integrin Receptors or any Other Protein Tyrosine Kinase Receptors, which are not Classified Under the Synthetic Small-molecules Inhibitors of the EGF receptor and/or VEGF receptor and/or integrin receptors or any other protein tyrosine kinase receptors, which are not classified under the synthetic small-molecules, which are of special interest, are the monoclonal antibodies directed to EGF receptor and/or VEGF receptor and/or integrin receptors or any other protein tyrosine kinase receptors. Representative compounds are, for example, atrasentan (integrin antagonist), rituximab, cetuximab, Avastin™ (bevacizumab), IMC-1C11, erbitux (C-225), DC-101, EMD-72000 (humanized EGF receptor-specific monoclonal antibody), vitaxin (antibody directed against the α, β$_3$ integrin), and imatinib (c-Kit inhibitor). Monoclonal antibodies which can specifically recognize their antigen epitopes on the relevant receptors, are in this respect of further special interest. The use of such antibodies, which were successful in vitro and in animal models, have not shown satisfying efficacy in patients as mono-drug therapy. Similar results were obtained when other anti-angiogenic or EGF receptor antagonists than antibodies were used in clinical trials. It seems that tumours, if some specific sites are blocked, may use other cell surface molecules to compensate for said original blocking. Thus, tumours do not really shrink during various anti-angiogenic or anti-proliferative therapies. For these reasons, combination therapies were in this case already proposed to circumvent this problem using, for example, monoclonal antibodies together with specific cytotoxic or chemotherapeutic agents or in combination with radiotherapy or radio-immunotherapy. Indeed, clinical trials have shown that these combination therapies are more efficient than the corresponding mono-administrations.

➢Inhibitors Directed to EGF Receptor and/or VEGF Receptor and/or Integrin Receptors or any Other Protein Tyrosine Kinase Receptors, which are Fusion Proteins A representative compound of this class is, for example, the compound with name VEGFtrap, developed by the pharmaceutical companies Regeneron and Aventis.

➢Compounds which Interact with Nucleic Acids and which are Classified as Alkylating Agents or Platinum Compounds Compounds which interact with nucleic acids and which are classified as alkylating agents or platinum compounds, have already been described for their use for the treatment of diseases of oncological nature. Representative classes and examples of compounds are melphalan, cyclophosphamide, oxazaphosphorines, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, nitrogen mustards (such as mechlorethamine), ethyleneimine compounds and alkyl-sulphonates.

➢Compounds which Interact with Nucleic Acids and which are Classified as Anthracyclines, as DNA Intercalators or as DNA Cross-linking Agents Compounds which interact with nucleic acids and which are classified as anthracyclines, as DNA intercalators (including DNA minor-groove binding compounds) or as DNA cross-linking agents are also of interest for the treatment of diseases of oncological nature. Representative classes and examples of compounds are daunorubicin, doxorubicin (adriamycin), liposomal doxorubicin (doxil), epirubicin, idarubicin, mitoxantrone, amsacrine, dactinomycin, distamycin and derivatives, netropsin, pibenzimol, mitomycin, CC-1065 (*Streptomyces zelensis* fermentation product), duocarmycins, mithramycin, chromomycin, olivomycin, phtalanilides (propamidine, stilbamidine), anthramycins, aziridines or nitrosoureas and their derivatives.

➢Anti-metabolites

Representative classes of anti-metabolites of interest are the pyrimidine and purine analogues or antagonists such as fluoropyrimidines and thiopurines, or inhibitors of the nucleoside diphosphate reductase. Representative compounds are, for example, cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid.

➢Naturally Occurring, Semi-synthetic or Synthetic Bleomycin Type Antibiotics (BLM-Group Antibiotics)

Representative classes and compounds of interest are the phleomycins, bleomycins, bleomycin derivatives and salts, CHPP, BZPP, MTPP, BAPP, liblomycin. These agents are believed to mediate their therapeutic effects via degradation of chromosomal DNA or RNA degradation (especially selective tRNA strand scission).

➢Inhibitors of DNA Transcribing Enzymes, Especially Topoisomerase I or Topoisomerase II Inhibitors A representative class and examples of compounds of interest are the acridines and acridine derivatives, rifamycins, actinomycins, adramycin, camptothecins (irinotecan or camptosar, topotecan), amsacrines and analogues, and the tricyclic carboxamides.

➢Chromatin Modifying Agents

A representative class of compounds of interest are the histonedeacetylase inhibitors, such as SAHA (suberoylanilide hydroxamic acid), MD-275, trichostatin A, CBHA (M-carboxycinnamic acid bishydroxamide), LAQ824, or valproic acid.

➢Mitosis Inhibitors, Anti-mitotic Agents, or Cell-cycle Inhibitors

Representative classes and examples of compounds of interest are the anti-cancer drugs from plants, such as the taxanes (paclitaxel or taxol, docetaxel or taxotere), the vinca alkaloids (navelbine, vinblastin, vincristin, vindesine or vinorelbine), the tropolone alkaloids (colchicine and derivatives), the macrolides (maytansine, ansamitocins, rhizoxin), the antimitotic peptides (phomopsin, dolastatin), the epipodophyllotoxins or the derivatives of podophyllotoxin (etoposide, teniposide), the steganacins and the antimitotic carbamate derivatives (combretastatin, amphetinile), or procarbazine. These compounds are cdk inhibitors, tubulin binders or inhibitors of the polo-like kinase.

➢Proteasome Inhibitors

A representative compound of interest belonging to this class is, for example, Velcade™ (bortezomib or PS-341).

➢Enzymes

Representative compounds and classes of interest are, for example, asparaginase, pegylated asparaginase (pegaspargase), and the thymidine-phosphorylase inhibitors.

➢Hormones, Hormone Antagonists or Hormone Inhibitors, or Inhibitors of Steroid Biosynthesis Representative classes and examples of hormones of interest are, for example, the gestagens and estrogens, such as estramustine or T-66, or megestrol. Representative classes and examples of hormone antagonists or inhibitors of interest are, for example, the anti-androgens, such as flutamide, casodex, anandron and cyproterone acetate, the aromatase inhibitors, such as amonogluthetimide, anastrozole, formestan and letrozole, the GNrH analogues, such as leuprorelin, buserelin, goserelin and triptorelin, the anti-estrogens, such as tamoxifen and especially its citrate salt, droloxifene, trioxifene, raloxifene, zindoxifene, the derivatives of 17β-estradiol (ICI 164,384 and ICI 182,780), aminoglutethimide, formestane, fadrozole, finasteride, or ketoconazole, or the LH-RH antagonist leuprolide. Steroid hormone inhibitors are especially suitable for the treatment of breast and prostate cancer.

➢Steroids

Representative compounds of interest are, for example, prednisone, prednisolone, methylprednisolone, dexamethasone, budenoside, fluocortolone and triamcinolone. The reasons why steroids may be used in the treatment of some cancers and the effects obtained with steroids in the treatment of cancer depends on the type of cancer to be treated. In the treatment of solid tumors, steroids are in first line used to control the symptoms. In the case of brain metastasis, they belong to the standard therapy for reducing oedema. They are also used to control the inflammation which surrounds the tumor lesions. In the treatment of haematologic malignant neoplasias of lymphatic cell lines (ALL, non-Hodgkin lymphoma, myeloma), due to their cytolytic effect, steroids are used as a real anti-tumor therapy, alone or in combination with classical chemotherapeutic agents. The naturally occurring steroid tetrahydrocortisol, the synthetic cyclodextrin derivative β-cyclodextrine tetradecasulfate and the tetracycline derivative minocycline, due to their antiangiogenic activity, have been suggested for a combination treatment with cytotoxic standard anticancer therapies, such as platinum, melphalan, cyclophosphamide, adriamycin, bleomycin or radiation based therapies (Teicher et al., Cancer research, Vol. 52, pp. 6702-6704, 1992). The steroid dexamethasone has also been tested as primary treatment of multiple myeloma (Dimopoulos et al., Blood, Vol. 80 (4), pp. 887-890, 1992). Furthermore, evaluation studies of combination therapies using dexamethasone and thalidomide, a substance known for its activity as TNF-α synthesis inhibitor and cytokine antagonist, have been disclosed recently. These studies focussed on previously untreated multiple myeloma (Weber et al., Journal of Clinical Oncology, Vol. 21, No. 1, pp. 16-19, 2003), newly diagnosed myeloma (Rajkumar et al., Journal of Clinical Oncology, Vol. 20, No. 21, pp. 4319-4323, 2002) and multiple myeloma after intensive chemotherapy (Ann. Oncol., Vol. 13, No. 7, pp. 1116-1119, 2002).

With regard to all aspects of the invention, suitable steroids for the combination treatment are meant to include in a non-limiting manner prednisone, prednisolone, methylprednisolone, dexamethasone, budenoside, fluocortolone and triamcinolone. The preferred steroid is dexamethasone.

➢Cytokines, Hypoxia-Selective Cytotoxins, Inhibitors of Cytokines, Lymphokines, Antibodies Directed Against Cytokines or Oral and Parenteral Tolerance Induction Agents Representative classes and examples of compounds of interest are interferons (especially interferon β), interleukins (especially IL-10 and 12), anti-TNFα antibodies (etanercept), Immunomodulatory drugs (or IMiDs, especially inhibitors of the TNF-α production, such as thalidomide, its R- and S-enantiomers and its derivatives, or revimid (CC-5013)), leukotrien antagonists, mitomycin C, aziridoquinones (BMY-42355, AZQ, EO-9), 2-nitroimidazoles (misonidazole, NLP-1, NLA-1), nitroacridines, nitroquinolines, nitropyrazoloacridines, "dual-function" nitro aromatics (RSU-1069, RB-6145), nitro aromatic deactivated mustards (CB-1954), N-oxides of nitrogen mustards (nitromin), metal complexes of nitrogen mustards, anti-CD3 or anti-CD25 antibodies, genetically modified enteric bacteria to achieve tolerance.

➢Supportive Agents

A representative class of compounds of interest are, for example, the biphosphonates and their derivatives, such as, for example, minodronic acid (YM-529, Ono-5920, YH-529), zoledronic acid monohydrate, ibandronate sodium hydrate, clodronate disodium. These compounds are in clinical development or have been recently approved for the treatment of bone metastasis from breast/lung cancer and for the treatment of multiple myeloma (Drugs of the Future 2002, 27 (10), pp. 935-941).

➢Chemical Radiation Sensitizers and Protectors

Representative classes and compounds of interest are, for example, the nitroimidazoles (metronidazole, misonidazole, benznidazole, nimorazole) and further nitroaryl compounds such as RSU-1069, the nitroxyl and N-oxides such as SR-4233, the halogenated pyrimidine analogues (bromodeoxyuridine, iododeoxyuridine), or the thiophosphates (for example WR-2721) as radiation protectors.

➢Photochemically Activated Drugs

Representative classes and compounds of interest are, for example, porfimer, photofrin, the benzoporphyrin derivatives, the pheophorbide derivatives, merocyanin 540 (MC-540), and tin etioporpurin.

➢Synthetic Poly- or Oligonucleotides

Synthetic poly- or oligonucleotides, which may optionally be modified or conjugated are also of interest. Representative classes of poly- or oligonucleotides are, for example, antitemplates RNAs and DNAs (synthetic or chemically modified oligonucleotides which are inactive per se but capable of competing with functional template-primers for their specific binding site on an enzyme and thereby blocking their functions), anti-sense RNAs and DNAs (sequence-specific inhibitors of protein synthesis which hybridize with complementary base sequences of a given m-RNA, such as oblimersen), especially directed against onco-genes, growth factor genes or tumor suppressor genes, antigene poly- or oligonucleotides (oligonucleotides capable of forming triplex DNA structures which selectively inhibit the transcription of a target gene), and ribozymes.

➢Non-Steroidal Anti-Inflammatory Drugs

Non-steroidal inflammatory drugs (NSAIDs) represent also an interesting class of compounds which may be used for a combination therapy within the meaning of the present invention. Cyclo-oxygenase (COX) inhibitors are of special interest, such as the non-selective COX inhibitors acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam and nimesulide or the pharmaceutically acceptable salts thereof, or the selective COX inhibitors meloxicam, celecoxib or rofecoxib. The selective COX-2 inhibitor meloxicam is especially preferred.

➤Other Chemotherapeutic or Naturally Occurring, Semi-Synthetic or Synthetic Therapeutic Agents Further classes and examples of compounds are of interest for a combination therapy within the meaning of the present invention, such as, for example, cytotoxic antibiotics, antibodies targeting surface molecules of cancer cells (especially HLA-DR antibodies such as, for example, apolizumab and 1D09C3), inhibitors of metalloproteinases (TIMP-1, TIMP-2), Zinc, inhibitors of oncogenes (especially c-myc, Ras, v-raf or c-src inhibitors, such as P53 and Rb), inhibitors of gene transcription (especially the inhibitors of the transcription factor complex ESX/DRIP130/Sur-2 which controls the expression of Her-2, such as those described in WO 03/097855) or of RNA translation or protein expression (especially the inhibitors of HER-2 expression, such as the heat shock protein HSP90 modulator geldanamycin and its derivative 17-allylaminogeldanamycin or 17-AAG), complexes of rare earth elements such as the heterocyclic complexes of lanthanides described for example in German Patent Nr. 101 38 538, photo-chemotherapeutic agents (PUVA, a combination of psoralen (P) and long-wave ultraviolet radiation (UVA)), IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamloxifen, testolactone.

In a preferred embodiment in accordance with the present invention, the further chemotherapeutic or naturally occurring, semi-synthetic or synthetic therapeutic agent is selected from synthetic small molecule VEGF receptor antagonists, small molecule growth factor receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids and which are classified as alkylating agents or platinum compounds, compounds which interact with nucleic acids and which are classified as anthracyclines, as DNA intercalators or as DNA cross-linking agents, including DNA minor-groove binding compounds, anti-metabolites, naturally occurring, semi-synthetic or synthetic bleomycin type antibiotics, inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists, hormone inhibitors, inhibitors of steroid biosynthesis, steroids, cytokines, hypoxia-selective cytotoxins, inhibitors of cytokines, lymphokines, antibodies directed against cytokines, oral and parenteral tolerance induction agents, supportive agents, chemical radiation sensitizers and protectors, photo-chemically activated drugs, synthetic poly- or oligonucleotides, optionally modified or conjugated, non-steroidal anti-inflammatory drugs, cytotoxic antibiotics, antibodies targeting surface molecules of cancer cells, and especially the HLA-DR antibodies such as, inhibitors of metalloproteinases, metals, inhibitors of oncogenes, inhibitors of gene transcription or of RNA translation or protein expression, complexes of rare earth elements, or photo-chemotherapeutic agents.

In a further preferred embodiment in accordance with the present invention, the further chemotherapeutic or naturally occurring, semi-synthetic or synthetic therapeutic agent is selected from a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl) oxy]-quinazoline, or a pharmaceutically acceptable salt thereof, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as Velcade™ (bortezomib or PS-341), an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17β-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-2721, a photo-chemically activated drug such as porfimer, photofrin, a benzoporphyrin derivative, a pheophorbide derivative, merocyanin 540 (MC-540) or tin etioporpurin, an anti-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam, nimesulide, meloxicam, celecoxib, rofecoxib, or a pharmaceutically acceptable salt of a non-steroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamloxifen or testolactone.

In a further preferred embodiment in accordance with the present invention, the further chemotherapeutic or naturally occurring, semi-synthetic or synthetic therapeutic agent is selected from an anti-cancer drug from plants such as paclitaxel (taxol), docetaxel or taxotere, a vinca alkaloid such as navelbine, vinblastin, vincristin, vindesine or vinorelbine, a vinca alkaloid such as navelbine, vinblastin, vincristin, vindesine or vinorelbine, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an immunomodulatory drug such as thalidomide, its R- and S-enantiomers and its derivatives, or revimid (CC-5013)), an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, a proteasome inhibitor such as Velcade™ (bortezomib or PS-341), a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, an antagonist of the mitogen-activated protein kinase such as BAY-43-9006 or BAY-57-9006, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, a quinazoline derivative such as 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a pharmaceutically acceptable salt thereof, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, or an antibody targeting the surface molecules of cancer cells such as apolizumab or 1D09C3.

In a further preferred embodiment in accordance with the present invention, the further chemotherapeutic or naturally occurring, semi-synthetic or synthetic therapeutic agent is selected from the above-mentioned quinazoline derivative disclosed in WO 02/50043 as exemplified compound of Example 1(10), namely 4-[(3-chloro-4-fluorophenyl) amino]-6-{[4-(N,N-dimethylamino)-1-oxo-2-buten-1-yl] amino}-7-((S)-tetrahydrofuran-3-yloxy)-quinazoline, or the tautomers, the stereoisomers and the salts thereof, particularly the physiologically and pharmaceutically acceptable salts thereof with inorganic or organic acids or bases.

In a further preferred embodiment in accordance with the present invention, the further chemotherapeutic or naturally occurring, semi-synthetic or synthetic therapeutic agent is selected from the di-maleic acid salt of the compound 4-[(3-chloro-4-fluorophenyl)amino]-6-{[4-(N,N-dimethylamino)-

1-oxo-2-buten-1-yl]amino}-7-((S)-tetrahydrofuran-3-yl-oxy)-quinazoline, or the tautomers or stereoisomers thereof.

In a further preferred embodiment in accordance with the present invention, the further chemotherapeutic or naturally occurring, semi-synthetic or synthetic therapeutic agent is selected from 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline or the physiologically and pharmaceutically acceptable salts thereof with inorganic or organic acids or bases.

Radiation Therapy, Radio-Immunotherapy or Pre-Targeted Radioimmunotherapy

Radiation therapy, radio-immunotherapy or pre-targeted radioimmunotherapy are used for the treatment of diseases of oncological nature. "Radiotherapy", or radiation therapy, means the treatment of cancer and other diseases with ionizing radiation. Ionizing radiation deposits energy that injures or destroys cells in the area being treated (the target tissue) by damaging their genetic material, making it impossible for these cells to continue to grow. Radiotherapy may be used to treat localized solid tumors, such as cancers of the skin, tongue, larynx, brain, breast, lung or uterine cervix. It can also be used to treat leukemia and lymphoma, i.e. cancers of the blood-forming cells and lymphatic system, respectively. One type of radiation therapy commonly used involves photons, e.g. X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons are machines that produce x-rays of increasingly greater energy. The use of machines to focus radiation (such as x-rays) on a cancer site is called external beam radiotherapy. Gamma rays are another form of photons used in radiotherapy. Gamma rays are produced spontaneously as certain elements (such as radium, uranium, and cobalt 60) release radiation as they decompose, or decay. Another technique for delivering radiation to cancer cells is to place radioactive implants directly in a tumor or body cavity. This is called internal radiotherapy. Brachytherapy, interstitial irradiation, and intracavitary irradiation are types of internal radiotherapy. In this treatment, the radiation dose is concentrated in a small area, and the patient stays in the hospital for a few days. Internal radiotherapy is frequently used for cancers of the tongue, uterus, and cervix. A further technique is intra-operative irradiation, in which a large dose of external radiation is directed at the tumor and surrounding tissue during surgery. Another approach is particle beam radiation therapy. This type of therapy differs from photon radiotherapy in that it involves the use of fast-moving subatomic particles to treat localized cancers. Some particles (neutrons, pions, and heavy ions) deposit more energy along the path they take through tissue than do x-rays or gamma rays, thus causing more damage to the cells they hit. This type of radiation is often referred to as high linear energy transfer (high LET) radiation. Radio-sensitizers make the tumour cells more likely to be damaged, and radio-protectors protect normal tissues from the effects of radiation. Hyperthermia, the use of heat, may also be used for sensitizing tissue to radiation. Another option involves the use of radio-labeled antibodies to deliver doses of radiation directly to the cancer site (radio-immunotherapy). There are numerous methods available in the art to link a radioisotope to an antibody. For example, for the radio-iodination of the antibody, a method as disclosed in WO 93/05804 may be employed. Another option is to use a linker molecule between the antibody and the radioisotope, e.g. MAG-3 (U.S. Pat. No. 5,082,930, EP 0 247 866), MAG-2 GABA (U.S. Pat. No. 5,681,927, EP 0 284 071), and N2S2 (phenthioate, U.S. Pat. No. 4,897,255, U.S. Pat. No. 5,242,679, EP 0 188 256). A further option is pre-targeted radio-immunotherapy, which may be used to minimize the radiation toxicity by separating the long-circulating antibody and the rapidly cleared radionuclide (Drugs of the future 2003, 28 (2), pp. 167-173). Detailed protocols for radiotherapy are readily available to the expert (Cancer Radiotherapy: Methods and Protocols (Methods in Molecular Medicine), Huddart R A Ed., Human Press 2002). The expert knows how to determine an appropriate dosing and application schedule, depending on the nature of the disease and the constitution of the patient. In particular, the expert knows how to assess dose-limiting toxicity (DLT) and how to determine the maximum tolerated dose (MTD) accordingly.

Co-Administration and/or Co-Treatment Therapies

Co-administration of the selected protein tyrosine kinase receptor antagonist and of the further chemotherapeutic or naturally occurring, semi-synthetic or synthetic therapeutic agent, and/or co-treatment with radiotherapy or radio-immunotherapy, is meant to include administration and/or treatment sequential in time or simultaneous administration and/or treatment. For sequential administration and/or treatment, the selected protein tyrosine kinase receptor antagonist can be administered before or after administration of the further chemotherapeutic or naturally occurring, semi-synthetic or synthetic therapeutic agent, and/or before or after treatment with radiotherapy or radio-immunotherapy.

The active compounds can be administered orally, bucally, parenterally, by inhalation spray, rectally or topically, the oral administration being preferred. Parenteral administration may include subcutaneous, intravenous, intramuscular and intrasternal injections and infusion techniques.

The active compounds can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents. Moreover, such oral pharmaceutical formulations can be suitably sweetened and/or flavoured by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages. Other suitable dosage forms for the compounds of this invention include controlled release formulations and devices well known to those who practice in the art.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatine and acacia. Additionally, lubricating agents such as magnesium stearate, sodium lauryl sulfate and talc or compositions of a similar type may also be employed as fillers in soft and hard-filled gelatine capsules; included lactose or milk sugar as well as high molecular weight polyethylene glycols. When aqueous suspensions and/or elixirs are desired for oral administration, the essential active ingredient therein may be combined with various sweetening or flavouring agents, colouring matter or dyes and, if so desired, emulsifying agents and/or water, ethanol, propylene glycol, glycerine and various like combinations thereof.

For purposes of oral administration, an especially suitable pharmaceutical formulation for the selected protein kinase receptor antagonist in accordance with the present invention is soft gelatine capsules. Suitable soft gelatine capsules for the encapsulation of pharmaceutical compounds and the process for their preparation are described, for example, in GB patent No. 395546, U.S. Pat. No. 2,720,463, 2,870,062, 4,829,057, and in the following publications: ANON (Verpack-Rundsch., Vol. 21, No. 1, January 1970, pp. 136-138), Lachman et al. (The Theory and Practice of Industrial Pharmacy, Chap. 13, published by Lea & Febiger, 1970), Ebert (Soft Gelatine Capsules: A Unique Dosage Form, reprint from Pharmaceutical Technology, October 1977) and R. F. Jimerson (Soft Gelatine Capsule Update, Drug Development and Industrial Pharmacy, Vol. 12 (8 & 9), pp. 1133-1144, 1986).

For purposes of parenteral administration, solutions of the compounds in sesame or peanut oil or in aqueous propylene glycol may be employed, as well as sterile aqueous solutions of the corresponding pharmaceutically acceptable salts. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these inject-able solutions to insure that the final products are obtained in a sterile condition.

For purposes of transdermal administration, the dosage form of the particular compound or compounds may include, by way of example, solutions, lotions, ointments, creams, gels, suppositories, rate-limiting sustained release formulations and devices therefore. Such dosage forms comprise the particular compound or compounds and may include ethanol, water, penetration enhancer and inert carriers such as gel-producing materials, mineral oil, emulsifying agents, benzyl alcohol and the like.

In accordance with one embodiment, the selected protein tyrosine kinase receptor antagonist, or its polymorph or pharmaceutically acceptable salt, may be administered in a daily dosage such that the plasma level of the active substance lies between 10 and 500 ng/ml for at least 12 hours of a 24 hours dosing interval.

In accordance with a further embodiment, the selected protein tyrosine kinase receptor antagonist, or its polymorph or pharmaceutically acceptable salt, may be administered in a daily dosage of between 2 mg and 20 mg/kg body weight.

The further chemotherapeutic or naturally occurring, semi-synthetic or synthetic therapeutic agent may be administered using suitable dosage forms, dosage levels and devices well known to those who practice in the art. In accordance with one embodiment, if the further chemotherapeutic or naturally occurring, semi-synthetic or synthetic therapeutic agent is a steroid, the steroid may be administered in a daily dosage of 5 to 500 mg.

As already mentioned hereinbefore, detailed protocols for radiotherapy are readily available to the expert. The expert knows how to determine an appropriate dosing and application schedule, depending on the nature of the disease and the constitution of the patient. In particular, the expert knows how to assess dose-limiting toxicity (DLT) and how to determine the maximum tolerated dose (MTD) accordingly.

In Vitro and In Vivo Combination Studies Showing the Potency to Inhibit the Proliferation and/or to Induce the Apoptosis of Tumour Cells In the following examples of combinations, in vitro experiments with representative cell lines or in vivo experiments with nude mice carrying specific tumours, illustrate the potency of the combination of a selected protein tyrosine kinase antagonist with a further chemotherapeutic agent and/or with radiotherapy to inhibit the proliferation of endothelial or tumour cells and/or to induce the apoptosis of tumour cells. These examples are thus illustrative of the present invention.

EXAMPLES OF COMBINATIONS

1. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof, and of a steroid, for the treatment of refractory or relapsed multiple myeloma In vitro studies performed with the monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone (compound MES(T)) have shown that this specific compound has unexpected properties which makes it especially suitable for the treatment of the diseases in accordance with the present invention, especially when combined with a steroid, and more specifically with dexamethasone.

Amongst these unexpected properties, the following are of particular relevance for the target indications: Tyrosine kinase inhibition of VEGFR1 to 3, FGFR1 and 3, PDGFR α; Inhibition of src-tyrosine kinase family members and potential inhibition of the proliferation of myeloma cells; Inhibition of the neo-angiogenesis induced by VEGF and bFGF; Inhibition of the paracrine IL-6 secretion; Inhibition of the cell contact mediated IL-6 secretion; Inhibition of the autocrine VEGF and bFGF effects; Direct induction of apoptosis on cell lines with t(4;14).

This specific compound appears to be further especially suitable for the treatment of multiple myeloma. The following recent findings constitute a line of evidence for the selection of this specific compound for this indication: Neovascularization parallels infiltration of bone marrow in a murine multiple myeloma model (Yaccoby et al., Blood 1998, Vol. 92 (8), pp. 2908-2913) and in multiple myeloma patients undergoing progression (Vacca et al., Blood 1999, Vol. 93 (9), pp. 3064-3073; Kumar et al., Blood 2002, Blood First Edition Paper, Pre-published Online Oct. 17, 2002, DOI 10.1182/blood-2002-08-2441); VEGF has been shown to be a potent stimulus of angiogenesis (Toi et al., Lancet Oncol. 2001, Vol. 2, pp. 667-673); VEGF is expressed in and secreted by multiple myeloma cells (Dankbar et al., Blood 2000, Vol. 95 (8), pp. 2630-2636; Bellamy et al., Cancer Res. 1999, Vol. 59 (3), pp. 728-33); VEGF induces IL-6 secretion from marrow stromal cells, which in turn augments VEGF expression from clonal plasma cells (Dankbar et al., Blood 2000, Vol. 95 (8), pp. 2630-2636); IL-6 is considered a major growth factor for multiple myeloma cells in vivo (Klein et al., Blood 1995, Vol. 85 (4), pp. 863-872); IL-6 inhibits Dexamethasone-induced myeloma cell death (Hardin et al., Blood 1994, Vol. 84 (9), pp.

3063-3070); VEGF induces proliferation and triggers migration of multiple myeloma cells (Podar et al., Blood 2001, Vol. 98 (2), pp. 428-435); VEGF enhances osteoclastic bone resorption, which is a characteristic feature of multiple myeloma (Nakagawa et al., FEBS Lett. 2000, Vol. 473 (2), pp. 161-164; Niida et al., J. Exp. Med. 1999, Vol. 190 (2), pp. 293-298); FGFR3 induces proliferation, inhibits apoptosis and is involved in progression of myeloma cells (Chesi et al., Blood 2001, Vol. 97 (3), pp. 729-736; Plowright et al., Blood 2000, Vol. 95 (3), pp. 992-998); FGFR3 is dysregulated and constitutively activated in a subset of myeloma patients (Chesi et al., Blood 2001, Vol. 97 (3), pp. 729-736; Chesi et al., Nat. Genet. 1997, Vol. 16 (3), pp. 260-264); Src family kinases are involved in proliferative responses induced in myeloma (Ishikawa et al.; Blood 2002, Vol. 99 (6), pp. 2172-2178).

The following results of in vitro experiments evidence that the properties of the compound MES(T) make it especially suitable for the treatment of multiple myeloma.

In the first experiment, the inhibition effect of the compound MES(T) on the secretion of IL-6 by bone marrow stromal cells (BMSC cells) was investigated, at different concentrations (0, 10, 50, 125, 250 and 500 nM) of MES(T), in native conditions (native) and in conditions of stimulation of the cells with the bFGF (+bFGF) or with the VEGF (+VEGF) growth factors. For comparison, the inhibition effect with inhibition of anti-bFGF (+anti-bFGF), anti-VEGF (+anti-VEGF) and a combination of anti-bFGF and anti-VEGF (+anti-VEGF+anti-bFGF) were also investigated. The results of the experiment are shown in the following Table II.

TABLE III

| | Inhibition of IL-6 secretion | | | |
|---|---|---|---|---|
| MES (T) concentration | BMSC mono-cultures | Transwell U-266 + BMSC co-cultures | Contact U-266 + BMSC co-cultures | U266 mono-cultures |
| 0 nM | 153.5 | 336.1 | 348.1 | 2.0 |
| 50 nM | 213.4 | 354.5 | | |
| 125 nM | 192.1 | 297.6 | 259.6 | |
| 250 nM | 69.9 | 231.1 | 199.4 | |
| 500 nM | 38.6 | 123.9 | 114.7 | |

The results of this experiment show that the compound MES(T) is able to decrease to its basal (native) value the level of IL-6 secretion of BMSC cultures stimulated by myeloma cells in transwell and contact co-cultures. Thus, it can be concluded that the compound MES(T) interferes with the myeloma-stroma interaction targeting the bone marrow microenvironment by significantly diminishing NFκB-dependent IL-6 production. This further shows the potency of the compound in accordance with the present invention for the treatment of multiple myeloma.

In further experiments, it could be shown that the compound MES(T) provides pro-apoptotic effects in t(14;16) MM1.s myeloma cells (MM1.s myeloma cells carrying the translocation t(14;16)), and that the compound MES(T) enhances the apoptosis induced by dexamethasone.

Due to these properties, it can be concluded that the compound MES(T) is especially suitable for a combination treat-

TABLE II

| | Inhibition of IL-6 secretion by BMSC cells | | | | | |
|---|---|---|---|---|---|---|
| MES(T) concentration | native | +bFGF | +VEGF | +anti-bFGF | +anti-VEGF | +anti-VEGF + anti-bFGF |
| 0 nM | 124.2 | 216.9 | 107.4 | 77.7 | 118.9 | 71.1 |
| 10 nM | 130.2 | 150.5 | 122.3 | 68.9 | 148.6 | 68.1 |
| 50 nM | 170.4 | 179.7 | 130.7 | 81.3 | 155.2 | 63.4 |
| 125 nM | 97.5 | 91.2 | 141.0 | 42.4 | 166.7 | 86.1 |
| 250 nM | 76.5 | 76.9 | 65.5 | 33.0 | 89.4 | 45.0 |
| 500 nM | 39.6 | 43.4 | 14.8 | 20.2 | 16.2 | 13.5 |

The results of this experiment show that the compound MES(T) at concentration of ≧250 nM inhibits basal (native) as well as bFGF/VEGF-stimulated IL-6 secretion of bone marrow stromal cells (BMSC cells), and that the inhibition is more potent than the inhibition obtained with the antibodies. Since the bFGF and VEGF growth factors (released by myeloma cells) have been previously shown to stimulate BMSC cells and the microvascular endothelium to produce and secrete IL-6, which itself stimulates myeloma cells to produce both the bFGF and VEGF growth factors, an inhibition of IL-6 secretion by the compound in accordance with the present invention shows its potency for the treatment of multiple myeloma.

In a further experiment, the inhibition effect of the compound MES(T) on the secretion of IL-6 in transwell and contact co-cultures of myeloma cells (U-266 myeloma cell lines) and bone marrow stromal cells (BMSC cells) was investigated, at different concentrations (0, 50, 125, 250 and 500 nM) of MES(T). For comparison, the inhibition effect on BMSC mono-cultures (native) and, as control, the level of secretion of U266 mono-cultures, were also investigated. The results of the experiment are shown in the following Table III.

ment of refractory or relapsed multiple myeloma with a steroid, and especially dexamethasone.

2. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof, and of a dual antagonist of the epidermal growth factor (EGF) receptor and of the human epidermal growth factor of type 2 (HE type 2) receptor, for the treatment of prostate cancer, non-small cell lung cancer or colorectal cancer The following experiment was performed in order to investigate the effect of a combination therapy with suboptimal doses of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, namely the di-chloride salt of (Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone (compound referred to as C12(T)), which is the di-chloride salt of above exemplified compound (T), and a dual antagonist of the epidermal growth factor (EGF) receptor and of the human epidermal growth factor of type 2 (HE type 2) receptor, namely the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, (compound referred to as EGFR/HER2 inh., and described in WO 02/50043 as exemplified compound of Example 1(10)), on the reduction of tumour growth, in comparison to the mono-therapies at the same doses.

Figure 3:
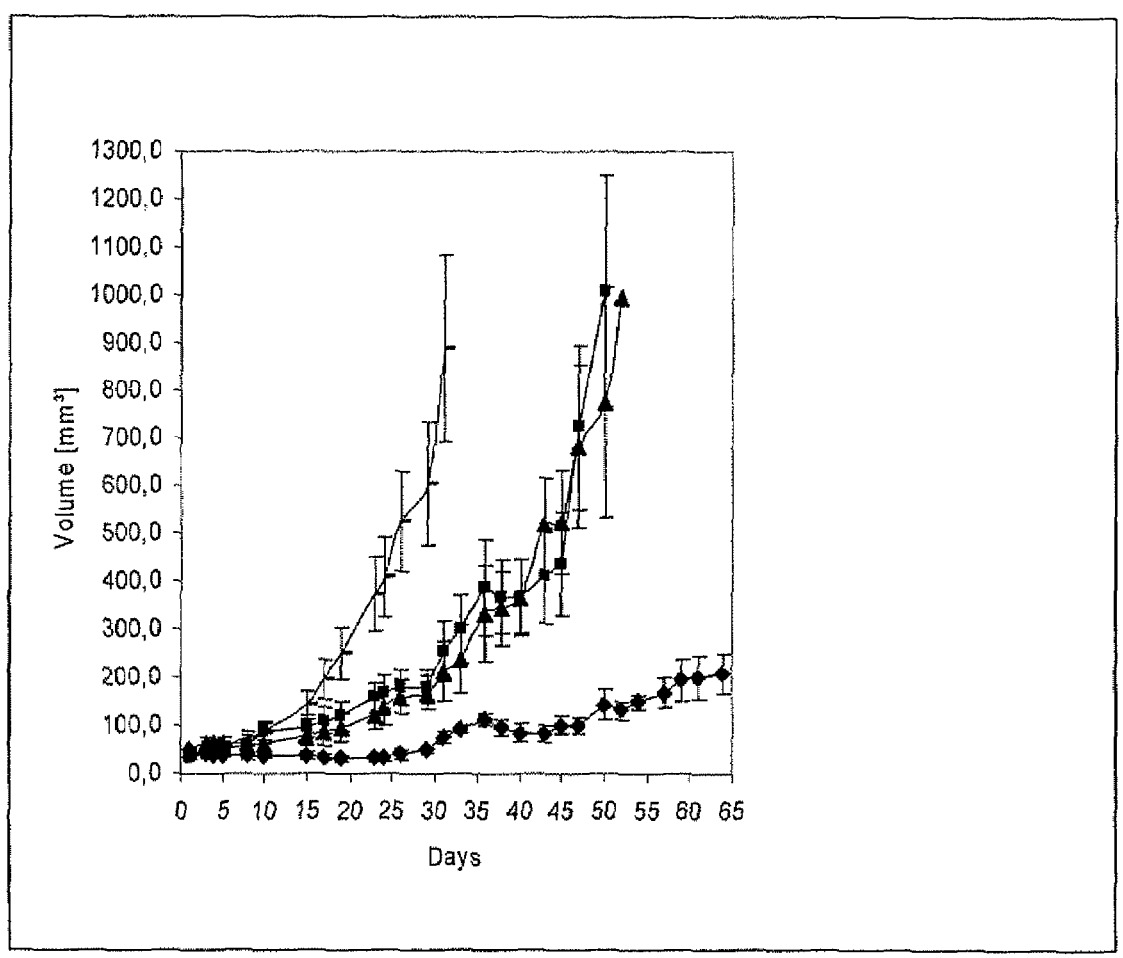

For this purpose, nude mice (NMRI nu/nu) were injected subcutaneously with SKOV-3 cells (human ovarian carcinoma). Mice carrying established tumours were randomised into control and treatment groups (N=10). The mice in the control group only received the carrier solution (0.5% Natrosol), the second group was treated daily per os with 15 mg/kg EGFR/HER2 inh., the third received once daily 50 mg/kg C12(T), and the fourth group of mice was treated with the combination of 15 mg/kg EGFR/HER2 inh. and 50 mg/kg C12(T). FIG. 3 shows the results of the experiment.

Daily per os treatment was initially performed for 31 days. At this time point some of the mice from the control group carried tumours bigger than 2000 mm³ and therefore had to be sacrificed. The calculated treated tumour to control tumour (T/C) ratio at this time point was 35% for the group treated with 15 mg/kg EGFR/HER2 inh., 32% for the group treated with 50 mg/kg C12(T), and 13% for the group treated with the combination. This result clearly demonstrates the anti-tumour effect of the combination of a VEGFR-2 and an EGFR/HER-2 inhibitor in vivo. Furthermore, continuing the treatment until day 64 shows extremely slow tumour growth in the combination group in comparison to the single treatment group where the tumours eventually are growing to comparable sizes as the control treated tumours.

From the results of this experiment, it can thus be concluded that the combination of compounds targeting different mechanisms involved in and important for tumour growth such as the VEGFR-2 inhibitor C12(T), inhibiting tumour angiogenesis, and the combined EGFR/HER-2 inhibitor EGFR/HER2 inh., inhibiting the proliferative signalling through the class I receptor tyrosine kinases, have a synergistic anti-tumour efficacy. Thus, all combinations of inhibitors of tumour angiogenesis (e.g. the indolinone derivatives described in WO 02/36564, WO 99/52869, WO 00/18734, WO 00/73297, WO 01/27080, WO 01/27081 or WO 01/32651, the small molecule VEGF receptor antagonists described in WO 01/60814, WO 99/48868, WO 98/35958, and especially the compounds vatalanib (PTK-787/ZK222584), SU-5416, SU-6668, SU-11248, SU-14813, AZD-6474, AZD-2171, CP-547632, CEP-7055, AG-013736, IM-842 or GW-786034, the monoclonal antibodies directed to the VEGF receptor, and especially Avastin™ (bevacizumab) or IMC-1C11) with EGFR inhibitors (e.g. iressa (ZD-1839), tarceva (OSI-774), PKI-166, EKB-569, HKI-272 or herceptin) or combined EGFR/HER-2 inhibitors (e.g. the quinazoline derivatives disclosed in WO 00/78735 and WO 02/50043, gefitinib, erlotinib, CI-1033 or GW-2016) will expectedly have the same or similar effects for anti-tumour therapies.

3. Combination treatment of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES(T)), and of radiation therapy for the treatment of breast cancer or ovarian cancer 4. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a further antagonist of VEGFR 2, PDGFR or bFGFR (e.g. vatalanib (PTK-787, ZD-6474, or the monoclonal antibody Avastin™) or an antagonist of EGFR (e.g. tarceva (OSI-774)), for the treatment of colorectal cancer, solid tumours, breast cancer, non-small cell lung cancer, small cell lung cancer or multiple myeloma 5. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of an antimetabolite (e.g. gemcitabine) and a platinum compound (e.g. cisplatin), or of an anticancer drug from plants (e.g. paclitaxel) and a platinum compound (e.g. carboplatin), for the treatment of non-small cell lung cancer or ovarian carcinoma 6. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of hormone antagonists (e.g. leuprorelin and flutamide), for a continuous and/or intermittent treatment of metastatic hormone sensitive prostate cancer 7. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a derivative of podophyllotoxin (e.g. etoposide) and a platinum compound (e.g. carboplatin or cisplatin), for the treatment of small cell lung cancer 8. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of an anticancer drug from plants (e.g. paclitaxel or taxol), for the treatment of ovarian carcinoma, small cell lung cancer or prostate cancer 9. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of an anticancer drug from plants (e.g. taxotere) for the treatment of prostate cancer 10. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a platinum compound (e.g. carboplatin) and an anticancer drug from plants (e.g. paclitaxel), for the treatment of ovarian carcinoma, especially after debulking surgery 11. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a topoisomerase I inhibitor (e.g. topotecan) and an anthracycline (e.g. doxorubicin), for the treatment of ovarian cancer 12. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a topoisomerase I inhibitor (e.g. topotecan), for the treatment of small cell lung cancer or ovarian carcinoma 13. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of an anticancer drug from plants (e.g. docetaxel) and a steroid hormone (e.g. estramustine), for the treatment of hormone refractory prostate cancer 14. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a vinca alkaloid (e.g. navelbine) for the treatment of lung cancer 15. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a platinum compound (e.g. carboplatin or cis-platin, preferably carboplatin) for the treatment of ovarian carcinoma or non-small cell lung cancer 16. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a COX-2 inhibitor (e.g. celecoxib, rofecoxib or meloxicam), for the treatment of colon or rectal cancer 17. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a 5-alpha reductase inhibitor (e.g. finasteride), for the treatment of prostate cancer 18. Combination of an antagonist of at least one receptor selected from VEGFR 1 to 3, PDGFRα and β, FGFR1, 2 and 3, EGFR, HER2, IGF1R, HGFR or c-Kit, which is further an antagonist of a src tyrosine kinase family member, or a polymorph, metabolite or pharmaceutically acceptable salt thereof (e.g. the compound MES (T)), and of a photo-chemotherapeutic agent (PUVA, a combination of psoralen (P) and long-wave ultraviolet radiation (UVA)), for the treatment of psoriasis Essentially, for the treatment of oncological diseases, the rationale for the combination treatment in accordance with the present invention is that there is a therapeutic advantage for the cancer patient to combine specific and mechanistically acting molecules with more broadly acting therapeutic concepts in the following ways:

Through the combination the target cells will have less chance to survive through possible escape mechanisms;

When compared to the doses used in a mono-therapy, due to an additive or synergistic effect of the combination, the required respective doses of the drugs can be reduced;

Scheduling of the respective drugs in a combination reduces the likelihood of the tumour cells to develop resistances against the drugs, leads to a better delivery of certain drugs to the tumour (reduction of intratumoral pressure) and may activate further death pathways in the tumour cells.

Thus, by targeting different cellular structures and compartments, the combination therapies in accordance with the present invention are expected to provide a clinically relevant benefit in survival or time to tumour progression for larger patient population as the corresponding mono-therapies. As a result of the specific anti-angiogenic therapy with, for example, the compound MES(T), tumours seem to be less capable of recovering from the damage caused by conventional chemotherapy. Also, by blocking the effects of VEGF on vascular permeability, a decline of the interstitial pressure in tumours seems to occur, allowing a greater penetration of the cytotoxic drugs. Maintenance therapy with a specific anti-angiogenic agent such as, for example, the compound MES (T), after standard cytoreduction, seems also to result in a consolidation of the response obtained with the cytotoxic therapy. This approach is substantiated by preclinical evidence that combinations of anti-angiogenic compounds with cytotoxic therapies result in synergistic anti-tumour activity.

For the treatment of non-oncological diseases, the rationale for the combination treatment in accordance with the present invention is also that there is a therapeutic advantage for the patient to combine specific and mechanistically acting molecules with more broadly acting therapeutic concepts. The expected effect of this combination is to avoid possible escape mechanisms for the target cells, to reduce the required respective doses of the drugs in comparison to the doses used in a mono-therapy (due to the additive or synergistic effect of the combination), and to reduce the likelihood of the target cells to develop resistances against the drugs.

LEGEND TO THE FIGURES

FIG. 1

Inhibition of VEGFR-2 phosphorylation after varying exposure of compound MES(T) on NIH3T3 KDR cells. The upper panel shows a Western blot probed with an antibody specific for phosphorylated tyrosine residues (α-PY). The lower panel shows a Western blot using an antibody specific for VEGFR-2 (α-KDR).

FIG. 2

Evolution of the tumour volume in nude mice bearing subcutaneous FaDu tumours, untreated (dotted line), treated orally twice weekly with a dose of 50 mg/kg of compound MES(T) (black line), or treated orally twice weekly with a dose of 100 mg/kg of compound MES(T) (gray line).

FIG. 3

Evolution of the tumour volume in nude mice bearing subcutaneous ovarian cancer SKOV-3 tumours, untreated (dashes), treated daily per os with 15 mg/kg EGFR/HER2 inh. (triangles), treated daily with 50 mg/kg C12(T) (squares), or treated with the combination of 15 mg/kg EGFR/HER2 inh. and 50 mg/kg C12(T) (losanges).

The invention claimed is:

1. A pharmaceutical combination comprising therapeutically effective amounts of:
   (i) (Z)-3-(1-(4-(N-((4-methyl-piperazin-1-yl)-methylcarbonyl)-N-methyl-amino)-anilino)-1-phenyl-methylene]-6-methoxycarbonyl-2-indolinone, or a pharmaceutically acceptable salt thereof; and
   (ii) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or a pharmaceutical acceptable salt the tautomers or the stereoisomers thereof;
wherein said pharmaceutical combination is optionally adapted for a co-treatment with radiotherapy or radio-immunotherapy, in the form of a combined preparation for simultaneous, separate or sequential use.

2. The pharmaceutical combination in accordance with claim 1, wherein (i) is 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or a pharmaceutically acceptable salt thereof.

3. The pharmaceutical combination in accordance with claim 2, wherein (i) is a monoethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone.

4. The pharmaceutical combination in accordance with claims 1, 2 or 3, wherein (ii) is quinazoline derivative 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or a pharmaceutically acceptable salt thereof.

5. The pharmaceutical combination in accordance with claims 1, 2 or 3, wherein (ii) is the di-maleic acid salt of the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline.

* * * * *